(12) United States Patent
von Oepen et al.

(10) Patent No.: US 12,036,119 B2
(45) Date of Patent: Jul. 16, 2024

(54) DELIVERY SYSTEM FOR HEART VALVE REPLACEMENT

(71) Applicant: Cephea Valve Technologies, Inc., Santa Clara, CA (US)

(72) Inventors: Randolf von Oepen, Aptos, CA (US); Hugo A. Cobar, Sunnyvale, CA (US); Francisco Valencia, East Palo Alto, CA (US); Russell Patrick Shelton, San Jose, CA (US); Henry Thek Chan, Sunnyvale, CA (US); Evelyn N. Haynes, Capitola, CA (US); Kim Lela Hayenga, San Mateo, CA (US); Curtis James Caton, Mountain View, CA (US); Gregory Matthew Hyde, Menlo Park, CA (US); Austin Michael Sherman, Cheshire, OR (US); Gabriel H. Monteon, Hollister, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 361 days.

(21) Appl. No.: 17/231,555

(22) Filed: Apr. 15, 2021

(65) Prior Publication Data

US 2021/0322166 A1     Oct. 21, 2021

Related U.S. Application Data

(60) Provisional application No. 63/012,762, filed on Apr. 20, 2020.

(51) Int. Cl.
*A61F 2/24* (2006.01)
*A61F 2/95* (2013.01)
(Continued)

(52) U.S. Cl.
CPC .......... *A61F 2/2433* (2013.01); *A61F 2/2436* (2013.01); *A61F 2/9524* (2020.05); (Continued)

(58) Field of Classification Search
CPC .... A61F 2/2433; A61F 2/2436; A61F 2/9524; A61F 2250/0098; A61F 2/9517; (Continued)

(56) References Cited

U.S. PATENT DOCUMENTS 7,097,690 B2 *   8/2006  Usher ................. A61M 5/1408
                                                                       604/9
11,045,311 B2 *  6/2021  Vaturi .................. A61F 2/2418
(Continued)

*Primary Examiner* — Sarah W Aleman
*Assistant Examiner* — Mikail A Mannan
(74) *Attorney, Agent, or Firm* — Workman Nydegger

(57) ABSTRACT

The present disclosure describes devices, systems, and methods for intravascularly delivering an implantable device to a targeted anatomical site such as the mitral annulus. A delivery system includes a delivery member coupled to a handle assembly and extending distally from the handle assembly. A delivery catheter is concentrically positioned within an outer member and configured to advance the intravascular device relative to the outer member. The delivery catheter includes a distal can structure configured to house at least a portion of the intravascular device in a compressed, pre-deployed position.

15 Claims, 36 Drawing Sheets

(51) Int. Cl.
  *A61L 2/00*   (2006.01)
  *A61M 5/14*   (2006.01)
  *A61M 25/00*  (2006.01)
(52) U.S. Cl.
  CPC ..... *A61F 2250/0098* (2013.01); *A61L 2/0094* (2013.01); *A61M 2005/1403* (2013.01); *A61M 2025/0019* (2013.01)
(58) Field of Classification Search
  CPC ............ A61F 2002/9534; A61F 2/2418; A61F 2002/9665; A61L 2/0094; A61M 2005/1403; A61M 2025/0019; A61M 25/0138; A61M 25/0147
  See application file for complete search history.

(56) References Cited

U.S. PATENT DOCUMENTS

| | | | |
|---|---|---|---|
| 11,273,038 B2* | 3/2022 | Tang | A61F 2/2466 |
| 2010/0286626 A1* | 11/2010 | Petersen | A61B 1/0055 |
| | | | 604/264 |
| 2013/0245732 A1* | 9/2013 | Jarl | B21D 35/001 |
| | | | 607/116 |
| 2014/0088692 A1 | 3/2014 | Wright | |
| 2016/0045311 A1 | 2/2016 | McCann et al. | |
| 2018/0028177 A1 | 2/2018 | Van et al. | |
| 2018/0055637 A1* | 3/2018 | von Oepen | A61B 17/00234 |
| 2018/0161557 A1* | 6/2018 | DeGraaf | B21F 45/008 |
| 2019/0091021 A1* | 3/2019 | Morrissey | A61F 2/2427 |
| 2020/0060849 A1* | 2/2020 | Inouye | A61B 17/12177 |
| 2020/0360141 A1* | 11/2020 | Stappenbeck | A61M 25/0147 |

* cited by examiner

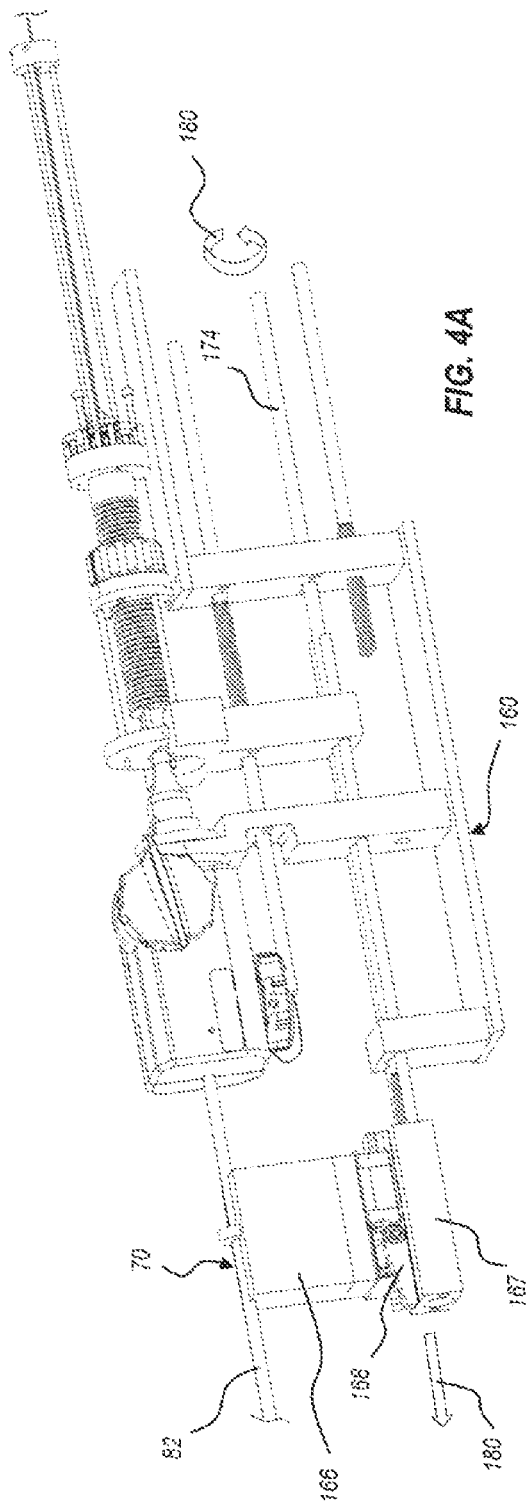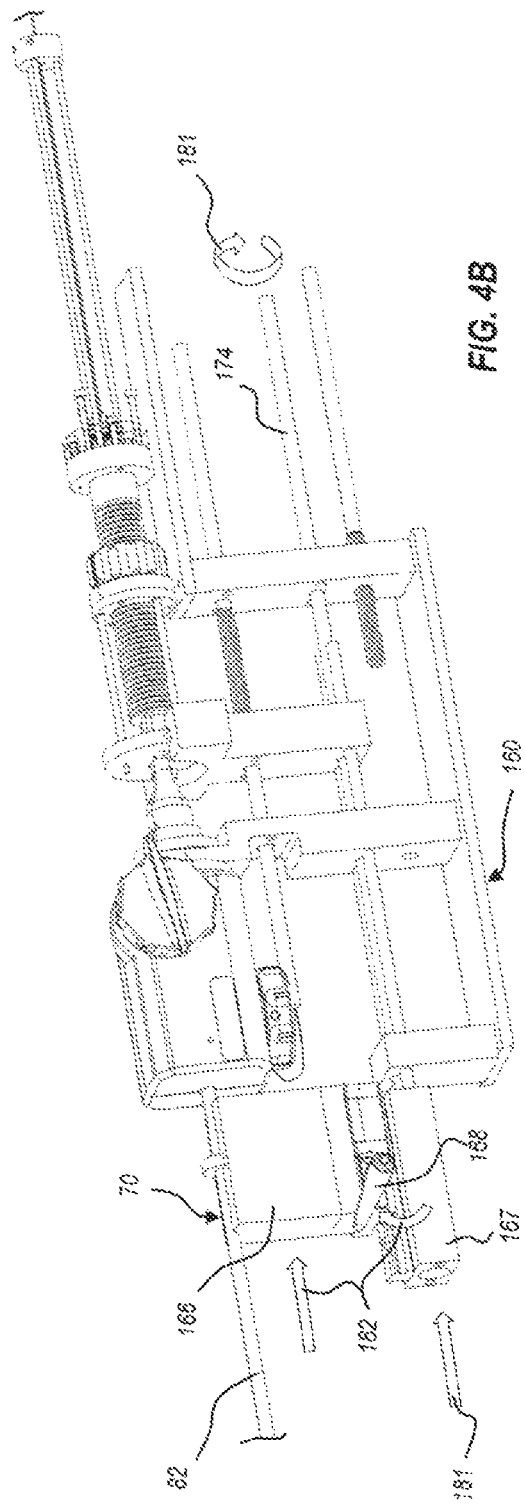

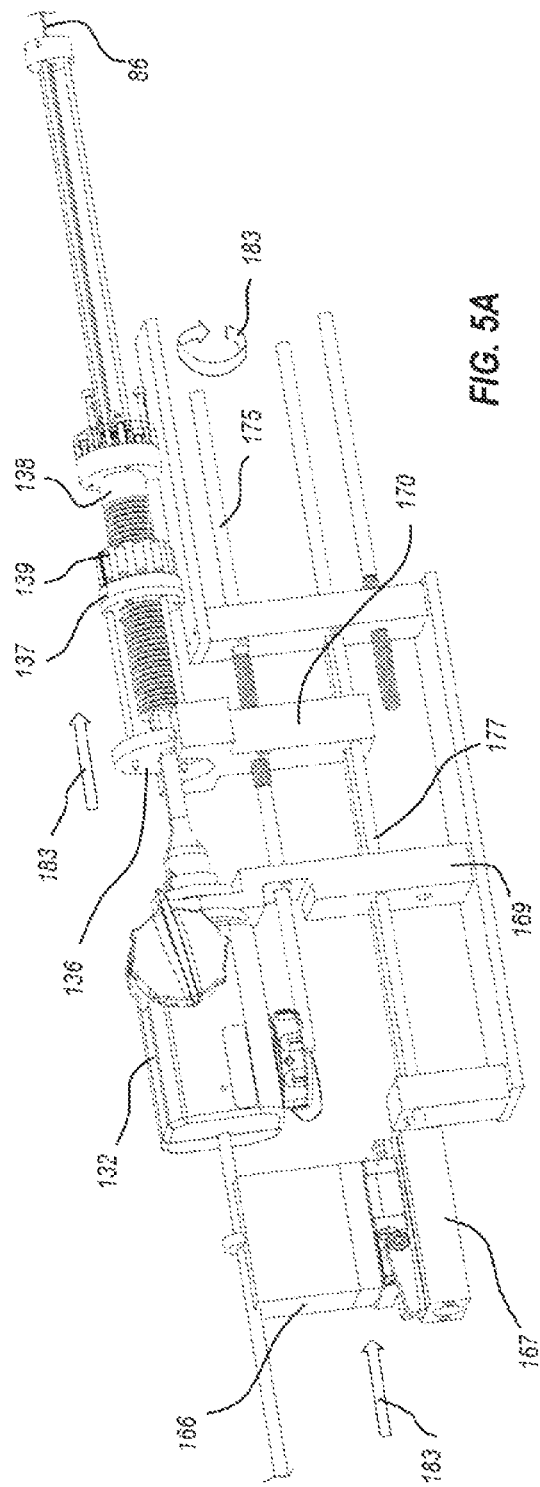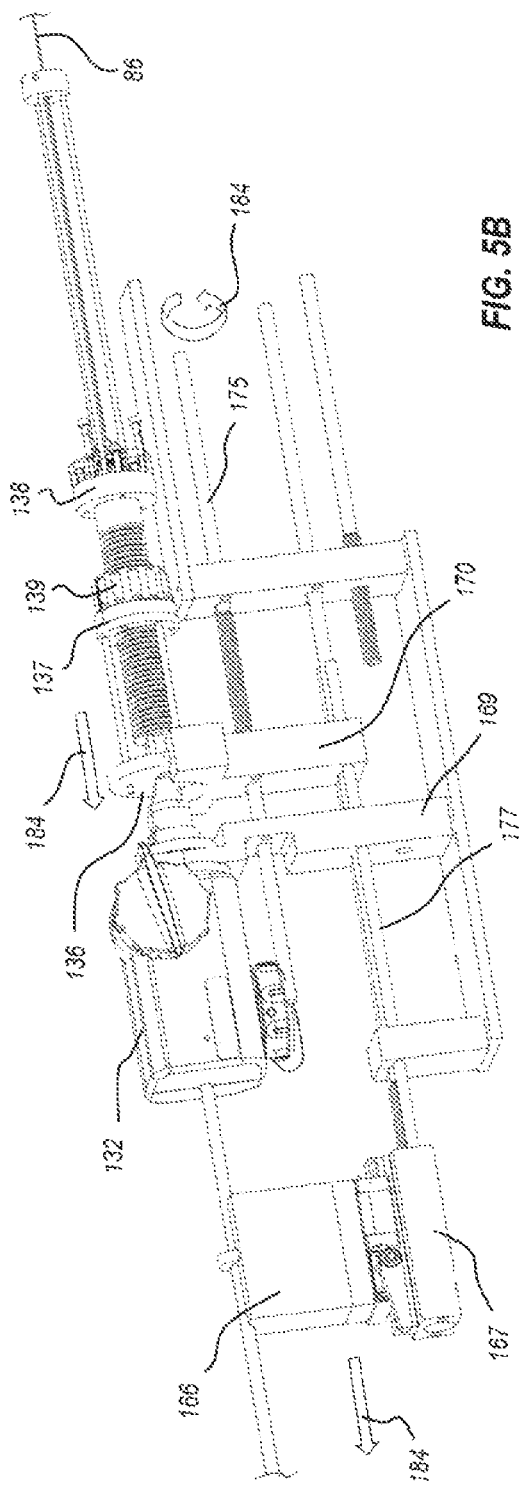

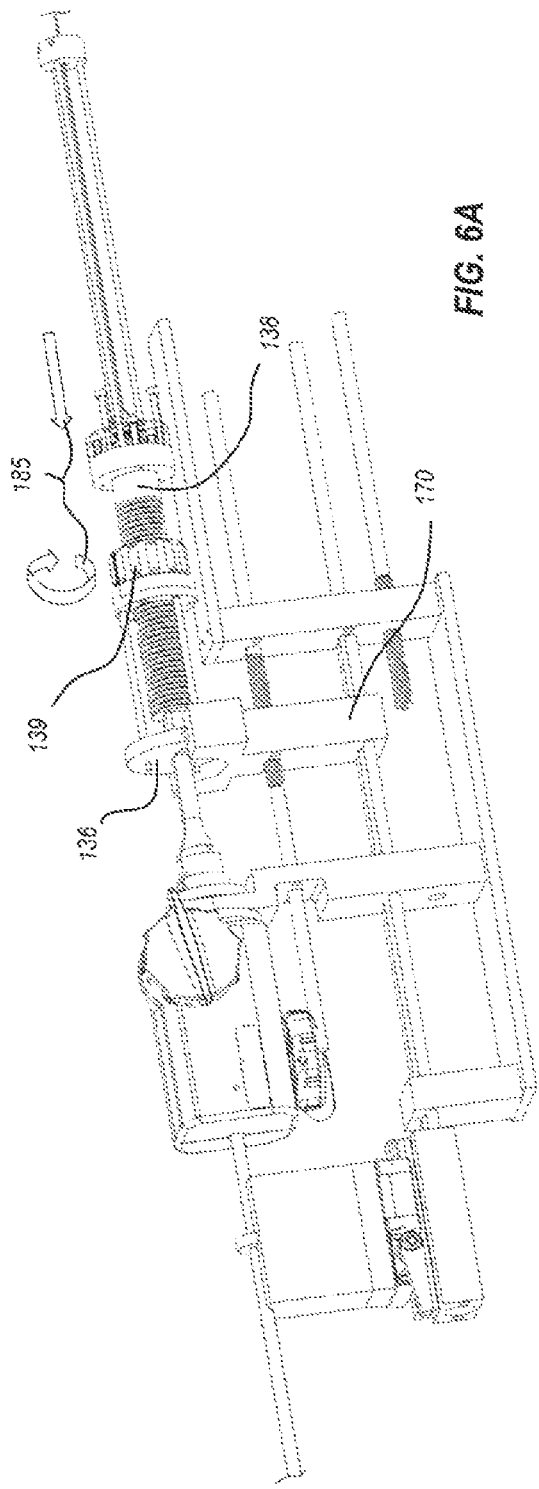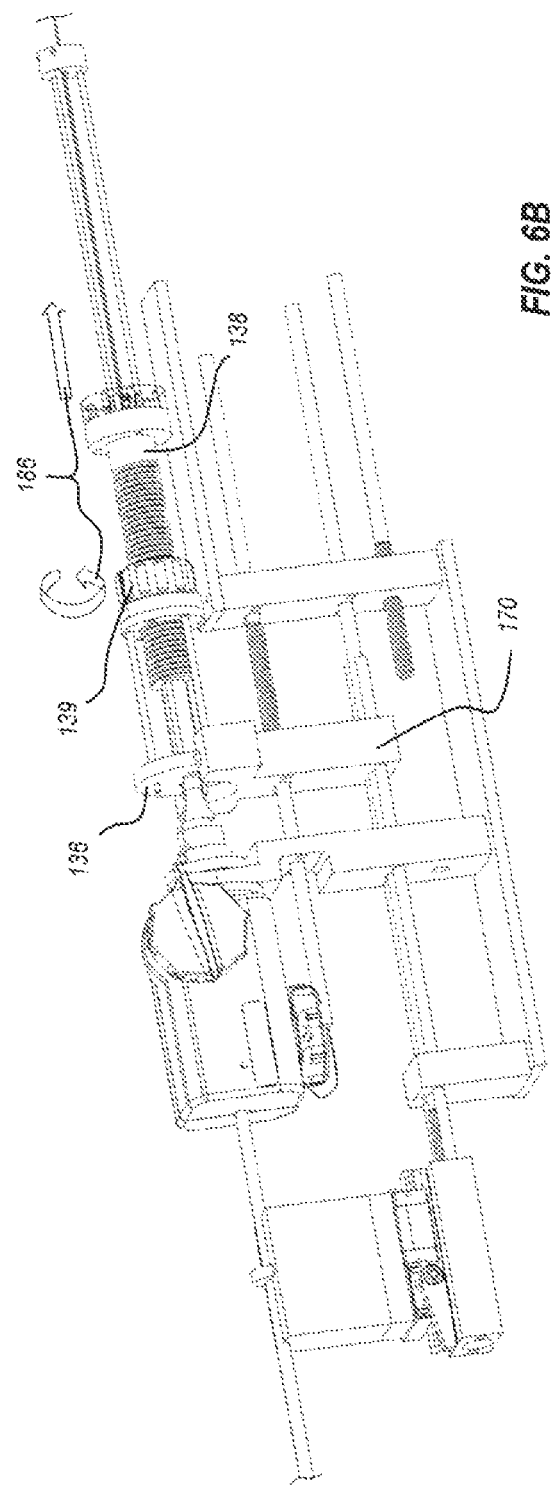

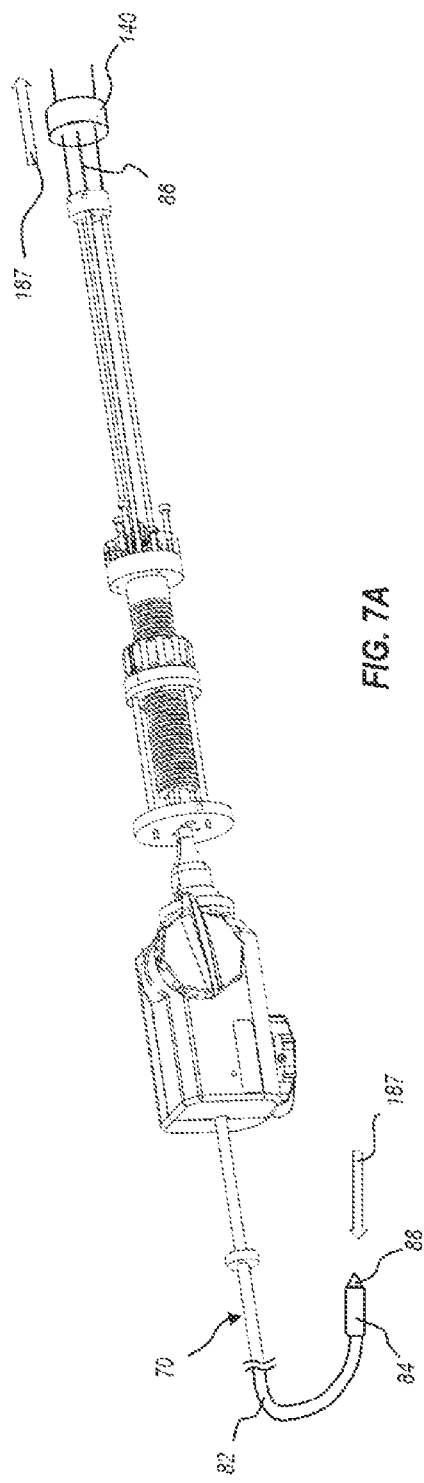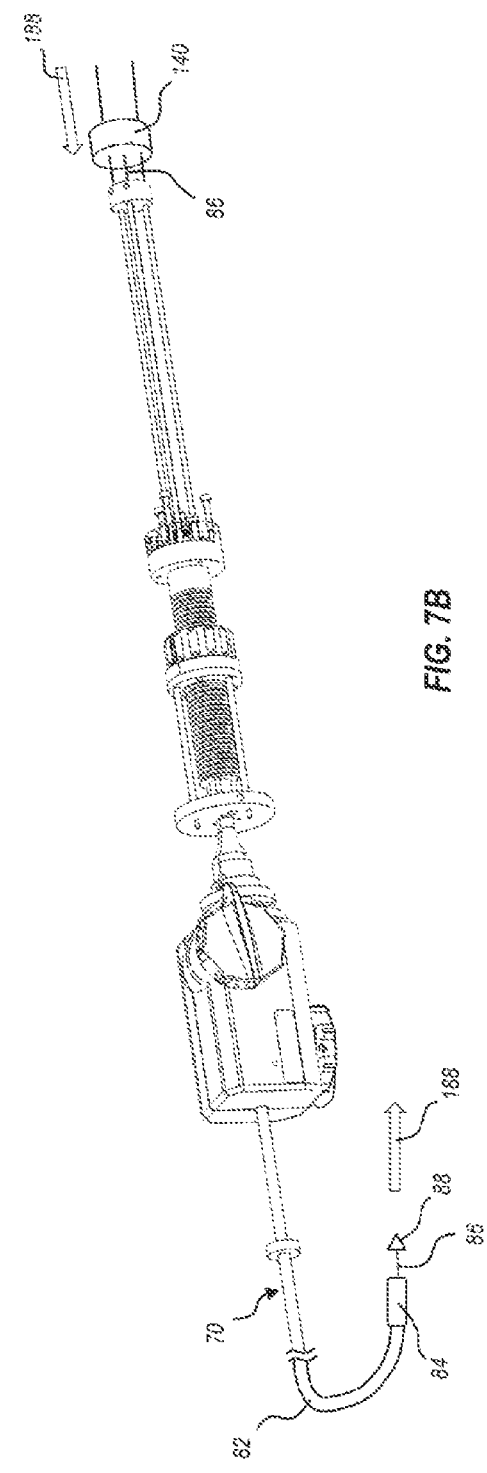

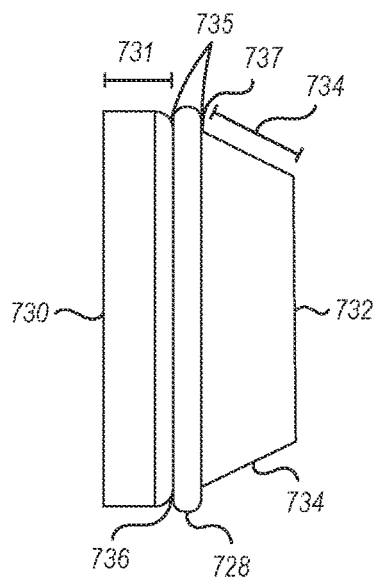
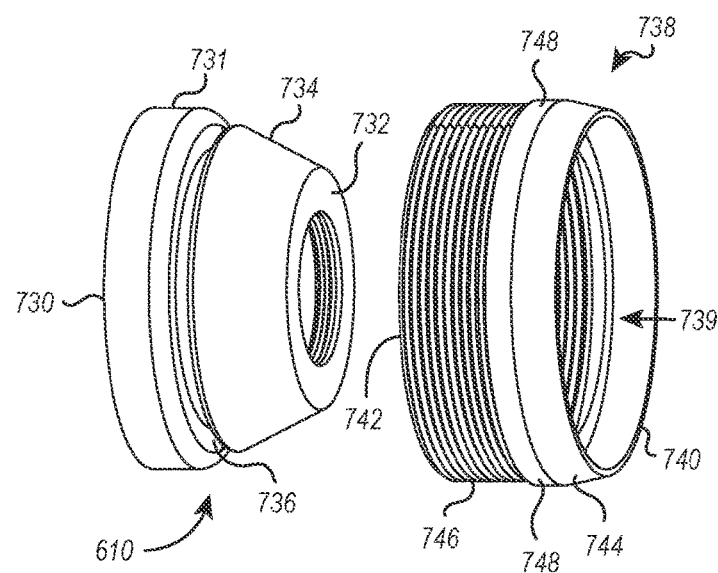
FIG. 19    FIG. 20A
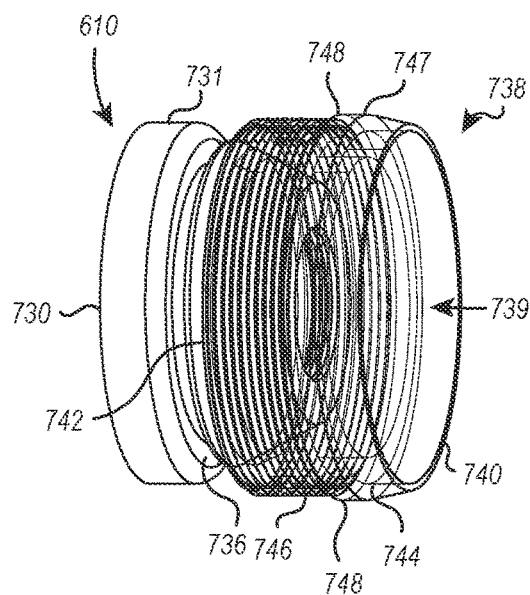
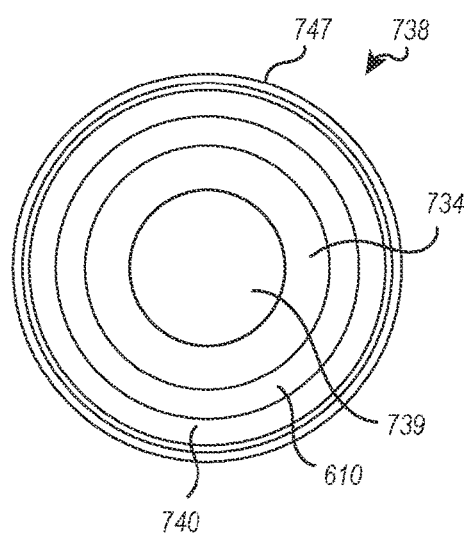
FIG. 20B    FIG. 20C

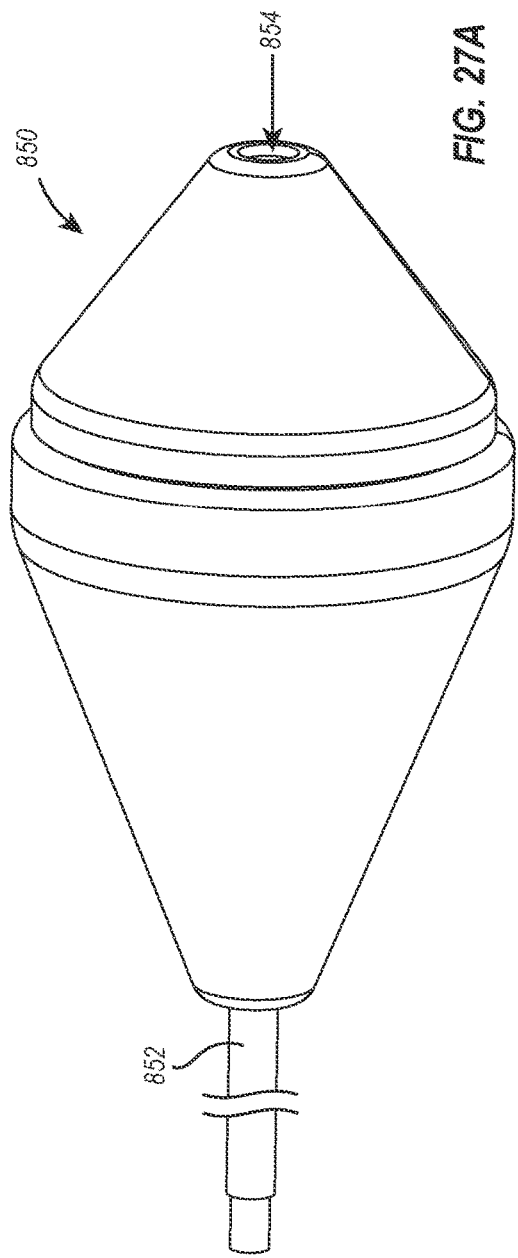
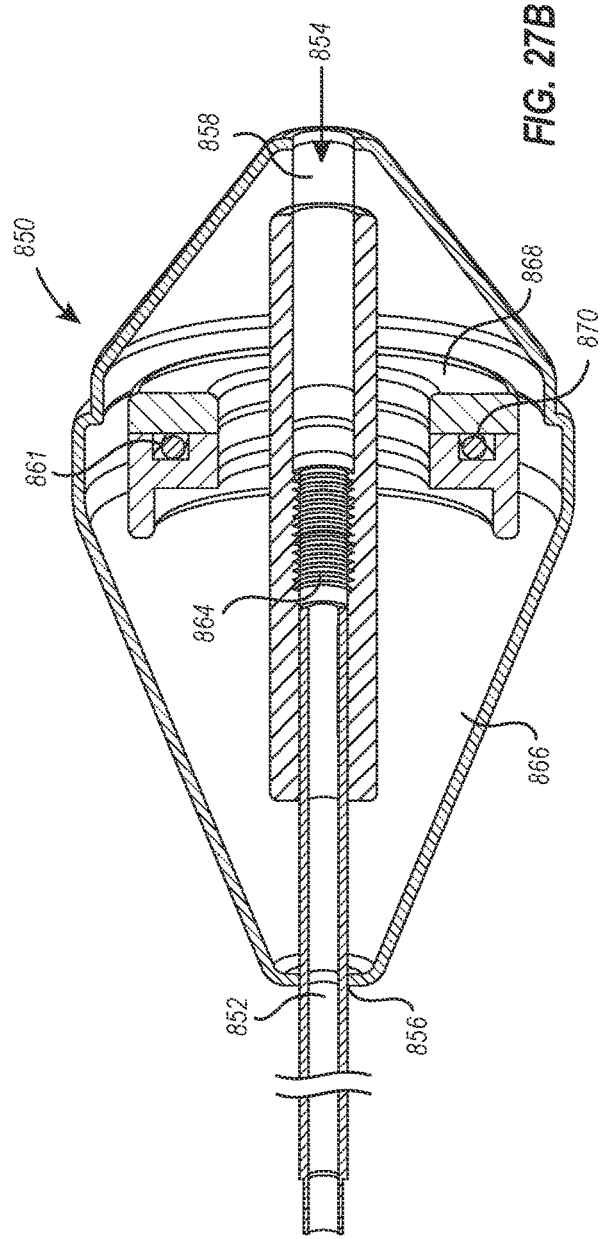

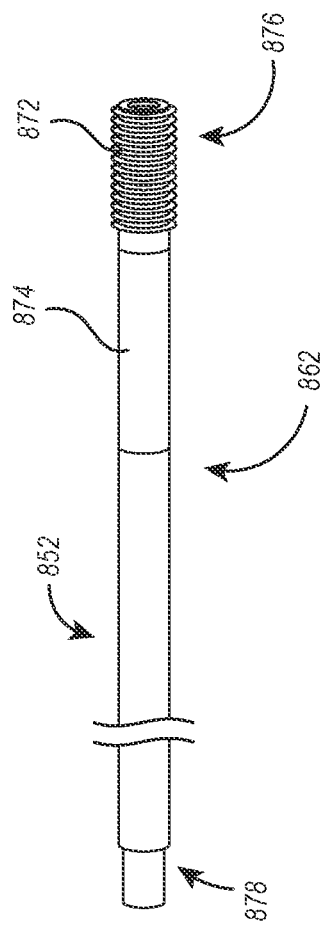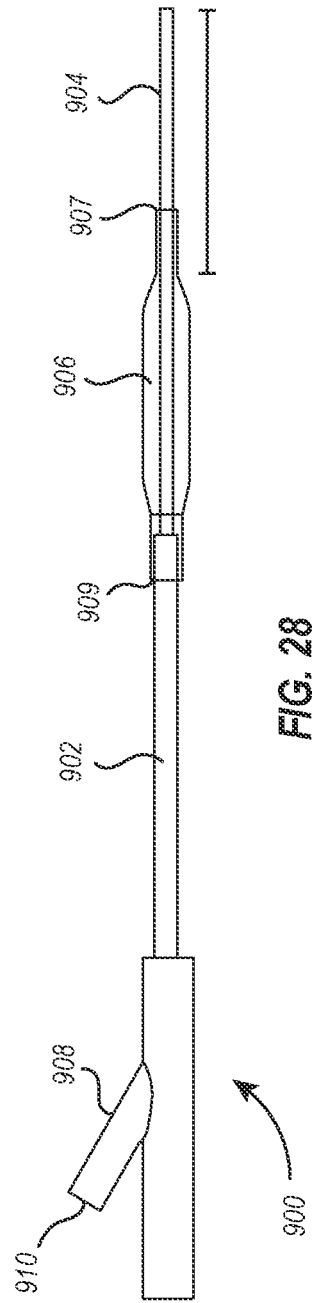

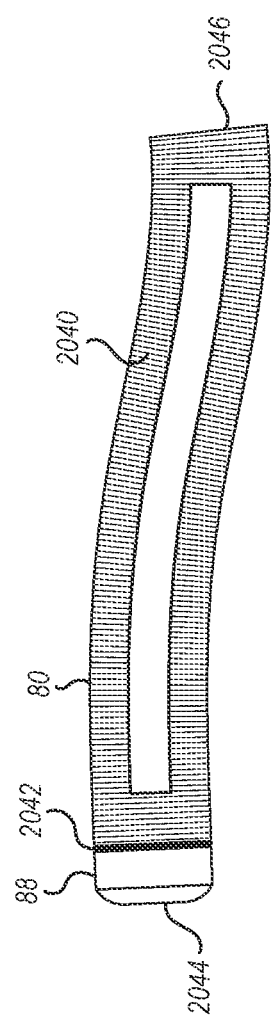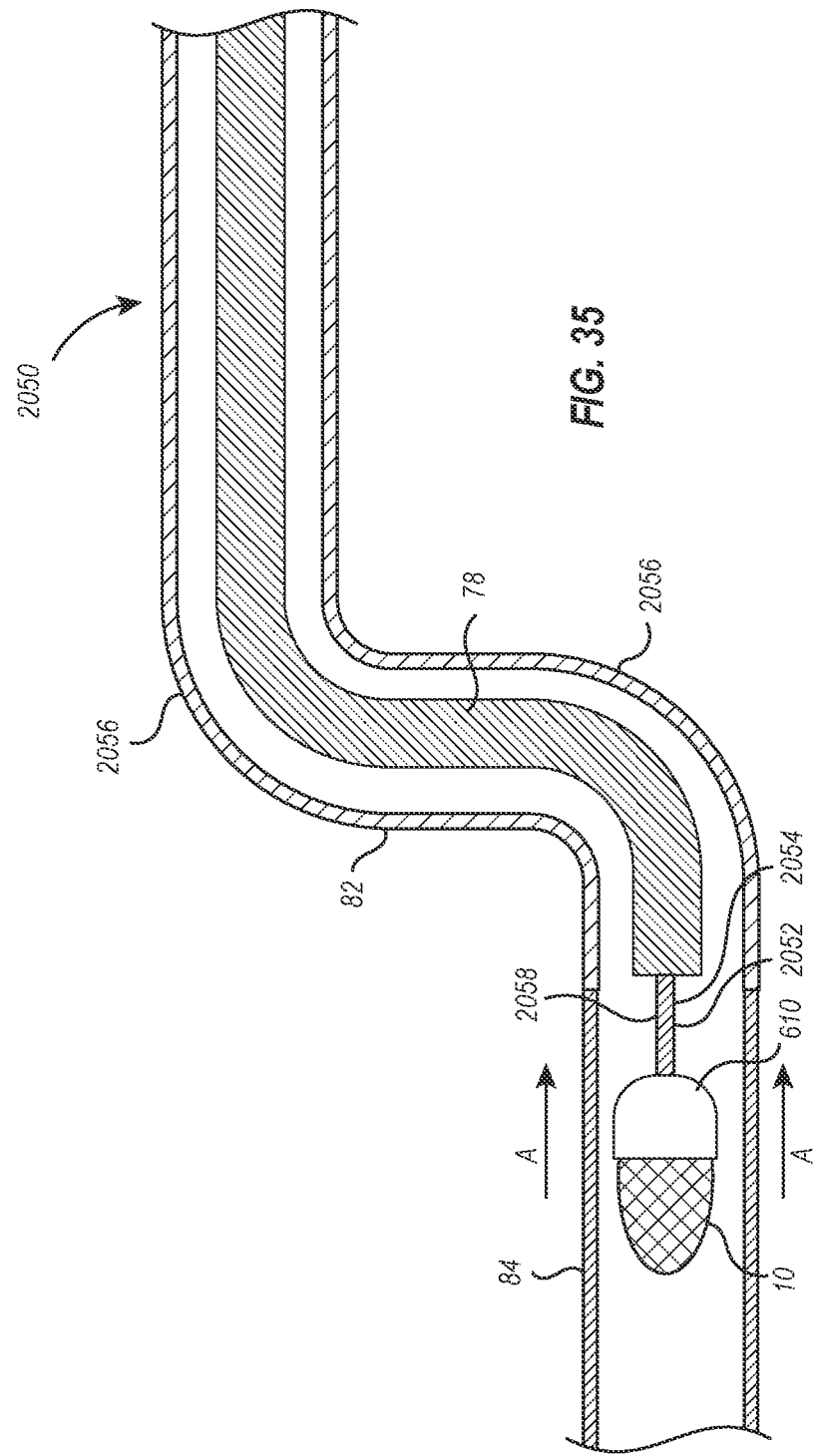

DELIVERY SYSTEM FOR HEART VALVE REPLACEMENT

CROSS-REFERENCE TO RELATED APPLICATIONS

This application claims the benefit of and priority to U.S. Provisional Patent Application Ser. No. 63/012,762, filed Apr. 20, 2020, the entire contents of which are incorporated by reference herein.

FIELD OF THE INVENTION

Embodiments of the present invention generally relate to a delivery system for heart valve replacement. More particularly, at least some embodiments of the invention relate to systems, hardware, software, computer-readable media, and methods for heart valve replacement.

BACKGROUND

1. Field of the Invention

The present disclosure generally relates to devices, systems, and methods for delivering an interventional device (sometimes referred to herein as an "IV device") to targeted anatomy such as at the mitral annulus.

2. The Relevant Technology

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication.

An example of an intravascular procedure that significantly reduces procedure and recovery time and cost over conventional open surgery is a heart valve replacement or repair procedure in which an artificial valve or valve repair device is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more deflecting mechanisms, which can be achieved by tension cable, or other mechanisms positioned inside the catheter. Precise control of the distal end of the catheter allows for more reliable and faster positioning of a medical device and/or implant and other improvements in the procedures.

An intravascularly delivered device needs to be placed precisely to ensure a correct positioning of the medical device, which is essential for its functionality, as the device may be difficult to reposition after the device is fully deployed from the delivery system. Additionally, the ability to recapture a partially deployed device is desirable in the event that the distal end of the catheter moves relative to the target location and compromises the precise positioning of the device.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 4A-4B, 5A-5B, 6A-6B, and 7A-7B illustrate various operations of the handle assembly to move components of the delivery member relative to one another;

FIG. 19 illustrates an alternate embodiment of a can of a delivery catheter with a radiopaque marker;

FIGS. 20A to 20C illustrate an alternate embodiment of a distal tip ring that may be utilized at the distal end of the steering catheter;

FIGS. 27A to 27C illustrate an alternate embodiment of an atraumatic distal tip of the delivery system that is attachable to, and detachable from the guidewire tube;

FIG. 28 illustrates an embodiment of a balloon catheter used to support the internal structure of a valve cover during crimping of the valve cover;

FIG. 34 illustrates an alternate embodiment of a steering catheter for reducing friction between a steering catheter and an outer sheath;

FIG. 35 illustrates an alternate embodiment of a delivery catheter incorporating an HSS coil;

SUMMARY

Figure 1:
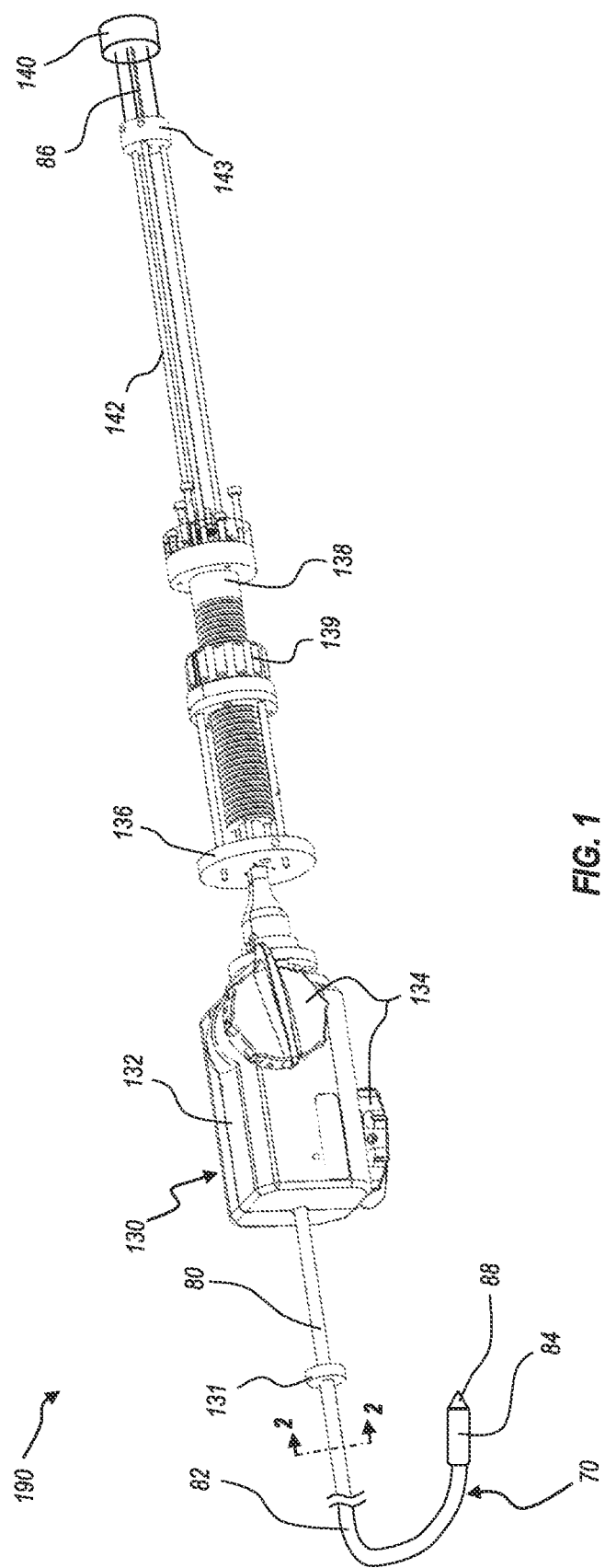
FIG. 1 illustrates a delivery system configured for delivering, positioning, and deploying an IV device, the delivery system including a handle assembly coupled to a delivery member.

Embodiments of the present disclosure solve one or more problems in the art with systems, methods, and devices for intravascular delivery of an interventional device to targeted intravascular anatomy, including a targeted cardiac valve. Suitable interventional devices that may be utilized in conjunction with the delivery system embodiments described herein may include valve repair devices, annuloplasty devices, valve clip devices, artificial heart valve devices, and other interventional devices. Embodiments described herein may be particularly useful for delivering interventional devices that move from a compressed, pre-deployed state to an expanded, deployed state.

In one embodiment, a delivery system includes an elongate delivery member having a proximal end and a distal end configured for housing the interventional device and including a plurality of coaxially positioned delivery member components. The delivery member components include a delivery catheter and an inner catheter (i.e., suture catheter) coaxially positioned within the delivery catheter. The inner catheter is adapted to maintain a connection with the interventional device until deployment of the interventional device.

The delivery system also includes a handle assembly for controlling movement of the delivery catheter and inner catheter. The handle assembly includes a delivery catheter holder to which a proximal end of the delivery catheter is attached, an inner catheter holder to which a proximal end of the inner catheter is attached, the inner catheter holder being disposed proximal of the delivery catheter holder, and a mechanical linkage (e.g., a lead rod) that fixes the relative positions of the delivery catheter holder and the inner catheter holder. The mechanical linkage enables the delivery catheter and the inner catheter to translate together relative to one or more other components of the delivery member.

The embodiments summarized above are each combinable with one another. Some embodiments may utilize one or more components of any of the embodiments summarized above and described in greater detail below.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

DETAILED DESCRIPTION OF SOME EXAMPLE EMBODIMENTS

The present disclosure is directed to devices, systems, and methods for loading, delivering, positioning, and deploying a replacement heart valve device. Throughout this disclosure, many examples are described in the context of a replacement artificial mitral valve. One of skill in the art will understand, however, that the described components, features, and principles may also be utilized in other applications. For example, at least some of the embodiments described herein may be utilized for loading, delivering, positioning, and deploying an artificial valve for replacing a pulmonary, aortic, or tricuspid valve.

Moreover, it will be understood that at least some of the delivery system embodiments described herein may be utilized in conjunction with other IV devices, including valve repair devices, annuloplasty devices, clip devices, and other IV devices not necessarily configured as a replacement valve. Thus, although the following description will typically refer specifically to a replacement mitral valve device, it will be understood that the same description may be applied to embodiments which utilize other suitable IV devices in other interventional procedures.

Notwithstanding such alternative applications, preferred embodiments described herein are configured to address challenges particularly associated with loading, delivering, positioning, and deploying an artificial replacement heart valve device. For example, where relatively simple catheters may be suitable for delivery of a clip or other such repair device, the larger size and/or more complex geometry of a replacement valve requires more robust delivery system features to properly load, deliver, and deploy the device. The embodiments described below are therefore particularly useful in for meeting the additional procedural challenges associated with heart valve replacement through an intravascular approach.

Delivery System Overview

FIG. 1 illustrates an exemplary embodiment of a delivery system 190. As shown, the delivery system 190 includes a handle assembly 130 and a delivery member 70. The delivery member 70 is coupled to the handle assembly 130 and extends distally from the handle assembly 130. The delivery member 70 includes a plurality of catheter and/or hypotube members which provide different functionality during operation of the delivery system 190 to enable effective delivery and deployment of an IV device.

The proximal end of an outer sheath 82 is coupled to an end ring 131, and the outer sheath 82 extends to a distal tip 88. A steering catheter handle 132 is disposed proximal of the end ring 131. The proximal end of a steering catheter 80 is coupled to the steering catheter handle 132, and the steering catheter 80 extends distally from the steering catheter handle 132 into the outer sheath 82. The steering catheter handle 132 includes one or more controls 134 which are operatively coupled to the steering catheter so that manipulation of the controls 134 adjusts the curvature of the steering catheter 80.

The outer sheath 82 extends to a distal end where it is coupled to a distal piece 84 (which may also be referred to herein as a "valve cover 84"). The distal piece 84 functions to house an IV device in a compressed, pre-deployed state during intravascular delivery of the device to the targeted cardiac site.

Because the steering catheter 80 is nested within the outer sheath 82, curving of the steering catheter 80 causes corresponding curving/steering in the outer sheath 82. The steering catheter 80 and outer sheath 82 may be referred to singly or collectively herein as the "outer member." The illustrated embodiment of the delivery member 70 includes additional components which are not visible in the view of FIG. 1 but may be seen in the cross-sectional view of FIG. 2.

Figure 2A:
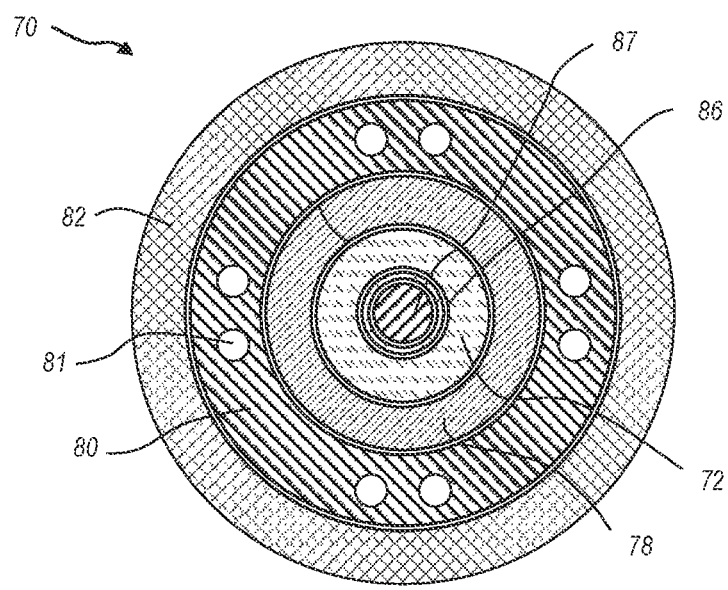
FIG. 2A illustrates a cross-sectional view of the delivery member showing various delivery member components that may be utilized, including a steering catheter and a delivery catheter disposed within and translatable within the steering catheter.
Figure 2B:
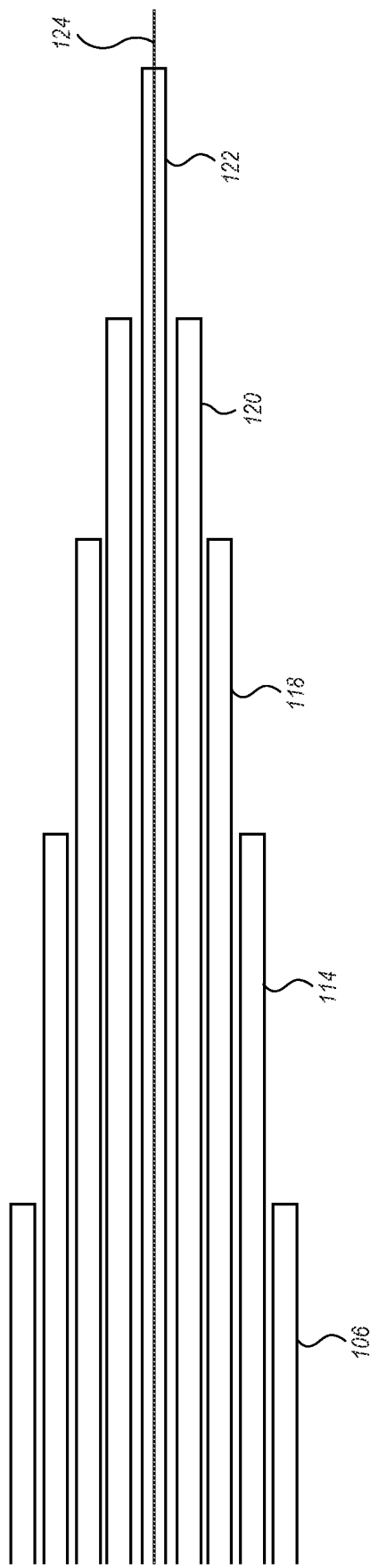
FIG. 2B illustrates another cross-sectional view of the delivery member.

FIG. 2 illustrates a cross-sectional view of the delivery member 70 taken along the cross-section line 2-2. As shown, the steering catheter 80 is disposed within the outer sheath 82. A delivery catheter 78 (or alternatively referred to herein as an extension catheter) is disposed within the steering catheter 80. An inner catheter 72 (also referred to herein as suture catheter 72) may be disposed within the delivery catheter 78, and a guidewire tube 86 may be disposed within the inner catheter 72. The guidewire tube 86 is configured for receiving a guidewire 87. Although the particular nested configuration shown in FIG. 2 represents one preferred embodiment, alternative embodiments may include a different concentric arrangement of constituent parts. For example, some embodiments may combine the steering catheter 80 and outer sheath 82 and/or configure the outermost member with steering functionality, some embodiments may include more than one catheter with steering functionality, etcetera.

The steering catheter 80 is configured to be selectively curved to allow intravascular navigation. In some embodiments, the steering catheter 80 provides steerability via a plurality of lumens 81 extending through the length of the steering catheter 80. The lumens 81 may be configured for receiving tension cables which extend between the controls 134 and the distal end of the steering catheter 80. One or more tension cables may additionally or alternatively be coupled to intermediate sections of the steering catheter 80.

Manipulation of the controls 134 therefore adjusts tension in the tension cables to increase or decrease curvature of the steering catheter 80 at various positions. Although the controls 134 are shown here as knobs, alternative embodiments may additionally or alternatively include one or more buttons, sliders, ratcheting mechanisms, or other suitable controls capable of adjusting tension to provide steering. Illustrative structures that can be used as part of the steering catheter handle 132 and or steering catheter 80 are described in U.S. Pat. No. 7,736,388, which is incorporated herein by this reference.

Referring again to FIG. 1, a delivery catheter holder 136 is disposed proximal of the steering catheter handle 132. Although not visible in the view of FIG. 1, the proximal end of the delivery catheter 78 is coupled to the delivery catheter holder 136. The delivery catheter 78 extends distally away from the delivery catheter holder 136 and into the steering catheter 80. An inner catheter holder 138 (also referred to herein as suture catheter holder 138) is disposed proximal of the delivery catheter holder 136. The inner catheter 72 may be coupled to the inner catheter holder 138 so that translation of the inner catheter holder 138 corresponds to translation of the inner catheter 72. For example, the inner catheter 72 may be selectively locked relative to the inner catheter holder 138 through a set screw, clamp, or other selective holding mechanism. The inner catheter 72 extends distally away from the inner catheter holder 138 and into the delivery catheter 78.

An inner catheter control 139 is operatively coupled to the inner catheter holder 138. Manipulation of the inner catheter control 139 adjusts the relative positioning of the delivery catheter holder 136 and inner catheter holder 138, and thus the relative positioning of the delivery catheter 78 and the inner catheter 72. In the illustrated embodiment, the inner catheter control 139 operates through threaded engagement with the inner catheter holder 138, such that rotation of the inner catheter control 139 translates the inner catheter holder 138 relative to the control 139 and therefore relative to the delivery catheter holder 136. Alternative embodiments may additionally or alternatively include one or more of a slider and rail assembly, a ratcheting mechanism, or other suitable means of linear adjustment.

The inner catheter 72 may extend proximally to and be attached to an inner catheter cap 143. A user may decouple the inner catheter 72 from the inner catheter holder 138 to allow movement of the inner catheter 72 by sliding/translating the inner catheter cap 143 along alignment rods 142. The guidewire tube 86 extends distally through the alignment cap 143 and into the inner catheter 72. The guidewire tube 86 extends to the distal end of the delivery member 70 where it is attached to a distal tip 88. The distal tip 88 is preferably formed from a flexible polymer material and provides an angled, atraumatic shape which assists in passing the delivery member 70 across the inter-atrial septum to the mitral annulus, which is required in a typical transfemoral approach to the mitral annulus.

In the illustrated embodiment, the guidewire tube 86 is coupled to a guidewire tube holder 140. By moving the guidewire tube handle, the guidewire tube 86 may be selectively translatable relative to the inner catheter cap 143 such that the guidewire tube 86 and distal tip 88 may be linearly translated relative to the inner catheter 72 and other components of the delivery member 70. The guidewire tube 86 may be selectively locked in longitudinal position relative to the inner catheter holder 138 and/or inner catheter cap 143, such as through a set screw, clamp, or other selective fastener. For example, such a fastening structure may be associated with the inner catheter cap 143.

When unlocked, the guidewire tube 86 (and likewise the distal tip 88) may be moved relative to the inner catheter 72. The ability to retract the distal tip 88 relative to the inner catheter 72 reduces the risk that the distal tip 88 will become overextended during deployment, where it could become tangled in chordae tendineae and/or cause injury to cardiac tissue. Additionally, independent movement of the guidewire tube 86 (with the distal tip 88) also allows for closing the gap between the distal tip 88 and the valve cover 84 following deployment of the intravascular device. When the intravascular device has been released, the distal tip 88 is separated from the valve cover 84 by a distance, such as by about 40 mm. To avoid drawing air into the catheter, the gap between valve cover 84 and distal tip 88 is closed by drawing the distal tip 88 towards the valve cover 88, preferably in the left side of the heart, to avoid sucking air into the catheter when pulled back into the right side of the heart (where there is relatively low pressure).

Figure 3:
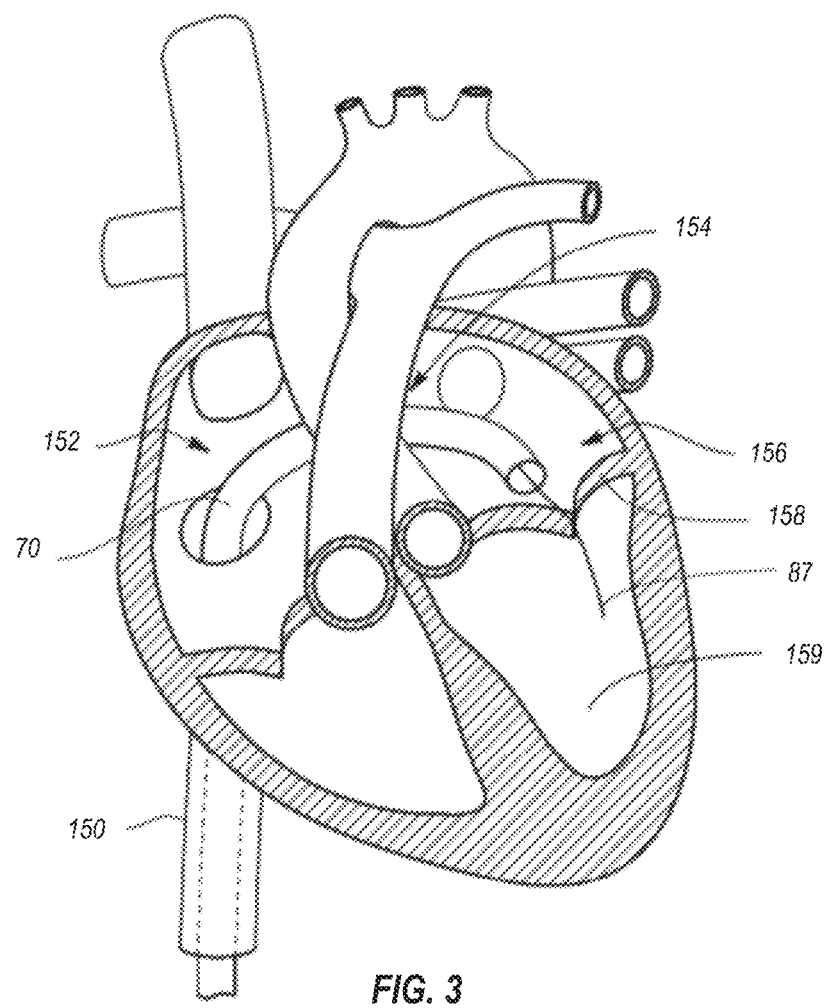
FIG. 3 illustrates an exemplary approach for delivering an IV device to the mitral annulus.

FIG. 3 illustrates a schematic representation of a patient's heart and a delivery procedure to the mitral annulus that may be conducted using the illustrated delivery system 190. The delivery member 70 may be inserted into the patient's vasculature (e.g., through a transfemoral approach) and directed to the inferior vena cava 150. The delivery member 70 is passed through the inferior vena cava 150 toward the heart. Upon entering the heart from the inferior vena cava 150, the delivery member 70 enters the right atrium 152. For mitral valve related procedures, the delivery member 70 must further pass into the left atrium 156 by passing through a puncture in the intra-atrial septum 154.

In other implementations, such as for procedures associated with a tricuspid valve, the delivery member 70 may be passed through the inferior vena cava 150 and into the right atrium 152, where it may then be positioned and used to perform the procedure related to the tricuspid valve. As described above, although many of the examples described herein relate to delivery to the mitral valve, one or more embodiments may be utilized in other cardiac procedures, including those involving the tricuspid valve.

Although a transfemoral approach for accessing a targeted cardiac valve is one preferred method, it will be understood that the embodiments described herein may also be utilized where alternative approaches are used. For example, embodiments described herein may be utilized in a transjugular approach, transapical approach, or other suitable approach to the targeted anatomy. For procedures related to the mitral valve or tricuspid valve, delivery of the artificial, replacement valve or other IV device is preferably carried out from an atrial aspect (i.e., with the distal end of the delivery member 70 positioned within the atrium superior to the targeted cardiac valve). The illustrated embodiments are shown from such an atrial aspect. However, it will be understood that the IV device embodiments described herein may also be delivered from a ventricular aspect.

In some embodiments, a guidewire 87 is utilized in conjunction with the delivery member 70. For example, the guidewire 87 (e.g., 0.014 in, 0.018 in, 0.035 in) may be routed through the guidewire tube 86 of the delivery member 70 to the targeted cardiac valve.

Additional details regarding delivery systems and devices that may be utilized in conjunction with the components and features described herein are described in United States Patent Application Publication Numbers 2018/0028177A1 and 2018/0092744A1, which are incorporated herein by this reference.

Operation of the Handle Assembly

FIGS. 4A and 4B illustrate in greater detail operation of a handle assembly (sometimes also referred to herein as a "control fixture") for controlling movement of various components of the elongated delivery member relative to one another, including for translating the outer sheath 82. Sheath movement may be utilized to deploy an IV device sheathed at or otherwise attached to the distal end of the outer sheath 82, or to recapture such an IV device by advancing the outer sheath 82 over the device. The illustrated embodiment provides two modes for translating the outer sheath 82. The outer sheath adjustor 174 and the slider block 167 are coupled to each other with corresponding threads, and rotation of the outer sheath adjustor 174 causes the slider block 167 to translate. With the slider lock 168 engaged, the outer sheath support 166 and outer sheath 82 move with the slider block 167. The slider lock 168 may also be disengaged, allowing the outer sheath support 166 and outer sheath 82 to be manually advanced or retracted by sliding relative to the slider block 167.

As shown by corresponding arrows 180, rotation of the outer sheath adjustor 174 in one direction causes the slider block 167 to advance, and as shown by corresponding arrows 181, rotation of the outer sheath adjustor 174 in the opposite direction causes the slider block 167 to retract. In FIG. 4A, the slider lock 168 is in an engaged position. In FIG. 4B, arrows 182 show disengagement of the slider lock 168 and translation of the outer sheath support 166 upon the slider block 167. The dual mode adjustment of the outer sheath 82 beneficially allows a user to make different types of adjustments depending on procedural circumstances and/or preferences. For example, a user may make larger, quicker adjustments by unlocking the slider lock 168 and manually sliding the outer sheath support 166, and may make finer, more controlled adjustments by rotation of the outer sheath adjustor 174.

FIGS. 5A and 5B illustrate a deployment adjustment that moves several of the delivery member components relative to the steering catheter 80. FIG. 5A illustrates, by arrows 183, rotation of the deployment adjustor 175 in a first direction to retract the slider block 167, delivery catheter holder 136, and suture catheter holder 138. FIG. 5B illustrates, by arrows 184, rotation of the deployment adjustor 175 in a second direction to advance the slider block 167, deployment catheter holder 136, and suture catheter holder 138. As explained below, after the steering catheter 80 has been curved to orient the delivery member 70 with respect to the mitral annulus, the other components of the delivery member 70 will need to be advanced over the steering catheter 80 to move into a proper position for deployment of the IV device. Holding the steering catheter 80 in place while the other components are advanced allows the compound curve of the steering catheter 80 to remain in the desired position.

The deployment adjustor 175 is threadedly engaged with the delivery catheter support 170. The connecting rods 177 mechanically link the delivery catheter support 170 to the slider block 167 to form a bracket assembly. The connecting rods 177 are able to freely pass through the steering catheter handle support 169 without engaging. The delivery catheter holder 136 and the suture catheter holder 138 are also mechanically linked as part of the bracket assembly by way of the alignment ring 137 and suture catheter control 139. Accordingly, rotation of the deployment adjustor 175 causes the delivery catheter holder 136, slider block 167, and suture catheter holder 138 to translate while the position of the steering catheter handle 132 is maintained. Translation of the outer sheath support 166 can be assured by locking to the slider block 167.

FIGS. 6A and 6B illustrate an operation for moving the suture catheter holder 138 relative to the delivery catheter holder 136. FIG. 6A shows, by arrows 185, that rotation of the suture catheter control 139 in a first direction causes the suture catheter holder 138 to advance relative to the delivery catheter holder 136. FIG. 6B shows, by arrows 186, that rotation of the suture catheter control 139 in a second direction causes the suture catheter holder 138 to retract relative to the delivery catheter holder 136. The threaded engagement of the suture catheter control 139 to the suture catheter holder 138 allows for finely controlled adjustments of the suture catheter position. As explained in more detail below, sutures of the suture catheter 72 (inner catheter 72) may be coupled to an IV device while the device is in a pre-deployed state, and movement of the suture catheter 72 relative to the delivery catheter 78 allows tension of the sutures to be adjusted.

Other embodiments that may be utilized in addition to or as an alternative to the suture catheter holder 138 and the suture catheter control 139 are provided below in the description of FIGS. 15B and 15C.

FIGS. 7A and 7B illustrate an operation for moving the guidewire tube 86 and guidewire tube holder 140 relative to the other components of the delivery member 70. FIG. 7A shows, by arrows 187, retraction of the guidewire tube holder 140 and corresponding retraction of the distal tip 88. FIG. 7B shows, by arrows 188 advancement of the guidewire tube holder 140 and corresponding advancement of the distal tip 88. The ability to adjust the distal tip 88 can lower the risk that the distal tip 88 undesirably interferes with chordae tendineae or other cardiac anatomy during deployment procedures. For example, during deployment of an IV device, the suture catheter 72 may be advanced to disengage from the IV device. If the distal tip 88 is not retracted relative to the advancing suture catheter 72, the distal tip 88 could extend too far into the ventricle where it could catch chordae tendineae and/or impinge against the cardiac wall.

Elongated Delivery Member Components

Figure 8:
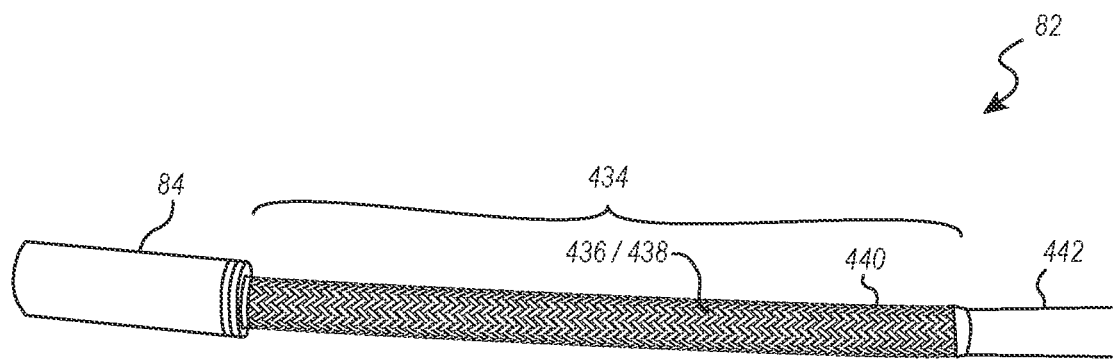
FIG. 8 illustrates the outer sheath, showing various sections that may be formed in the outer sheath.
Figure 9:
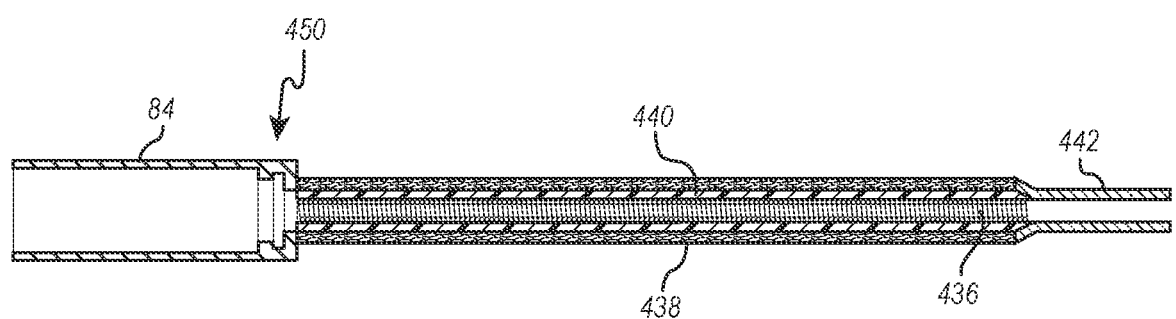
FIG. 9 is a cross-sectional view of the outer sheath of FIG. 8.
Figure 10:
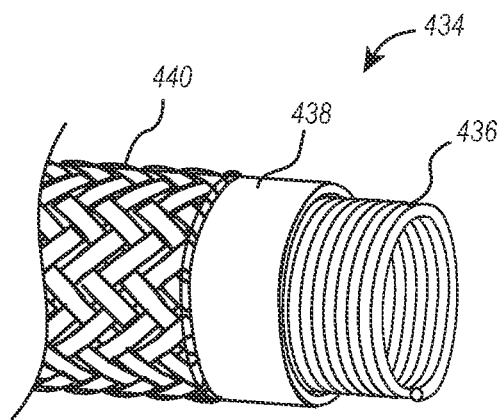
FIG. 10 is a partial cut-away view of an intermediate portion of the outer sheath.

FIGS. 8 and 9 illustrate a portion of the distal end of the outer sheath 82 and distal piece 84 (also occasionally referred to herein as cover 84). Distal piece 84 can be formed as a cylindrical tube having an inner diameter and length sized to receive the IV device, in a collapsed/pre-deployed configuration, within the lumen of distal piece 84. Distal piece 84 can include a plurality of microfabricated cuts (e.g., laser cuts) and a pair of continuous longitudinal spines located on opposite sides so that distal piece 84 can bend and flex substantially in a single plane. The outer sheath 82 can also include a bending portion 434 that can be attached to and located proximal to distal piece 84. Bending portion 434 may have a sufficient length to surround and extend along that portion of the delivery system that is designed to bend and reorient, via the steerable catheter 80, to navigate through a patient's vasculature and/or heart to a target site for deploying the IV device. In some embodiments, the bending portion 434 can include a cable tube or coil 436 surrounded by a braided structure 438 (sometimes collectively referred to as the "coil/braid portion 436/438") as shown in FIG. 10.

Attached to the proximal end of bending portion 434 is a cut hypotube 442 that extends from bending portion 434 to the proximal end of the sheath 82. Hypotube 442 can include a plurality of slits and at least one longitudinally continuous spine that can preferably be continuous and uninterrupted along a longitudinal length of, and located at a fixed angular location on, hypotube 442.

In such embodiments, it can be desirable for the bending portion 434 of delivery catheter to remain liquid tight. To seal the bending portion 434, a flexible, fluid impermeable covering can be provided over the coil/braid portion 436/438, extending from the distal piece 84 to a location proximal the coil/braid portion 436/438. For example, the delivery sheath 82 can also include a thin walled flexible cover 440 that extends from the distal piece 84 to the hypotube 442. Flexible cover 440 can be bonded at each end to the underlying structure, using one of a variety of different adhesives, thermal adhesives, UV bonded adhesive, or other techniques.

Figure 17:
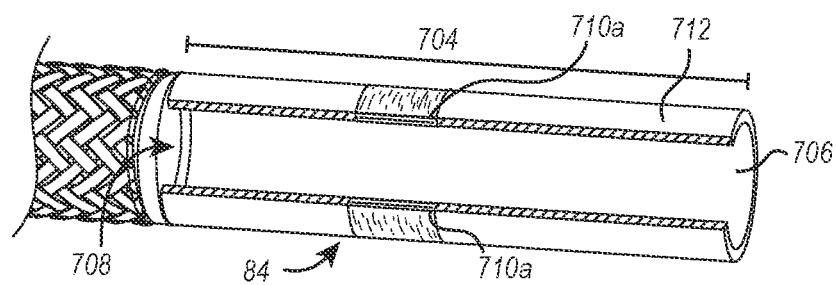
FIG. 17 illustrates a valve cover having a radiopaque guide line or marker.

Additional details and embodiments related to the cover 84/distal piece 84 are described below in the section titled "Echo Visualization of the Valve Cover" and are also shown in part by FIG. 17. Additional details and embodiments related to the hypotube 442 are described below in the section titled "Reducing Friction between Delivery Catheter and Suture Catheter" and are also shown in part in FIG. 30.

Referring again to FIG. 9, outer sheath 82 can also be coupled to distal piece 84 via a swivel connection, generally indicated at 450. To overcome the challenging forces that can develop during insertion of a relatively large delivery catheter into the vasculature of a patient, swivel connection 450 allows rotation of outer sheath 82 by a few degrees, back and forth (i.e., alternating between clockwise rotation and counter-clockwise rotation) while at the same time moving the delivery system 400 in a generally longitudinal direction. This rotational motion (during simultaneous longitudinal translation) helps to overcome some of the longitudinal forces that may resist insertion of outer sheath 82 through a patient's vasculature or frictional forces between the outer sheath 82 and the steering catheter 80.

Figure 11:
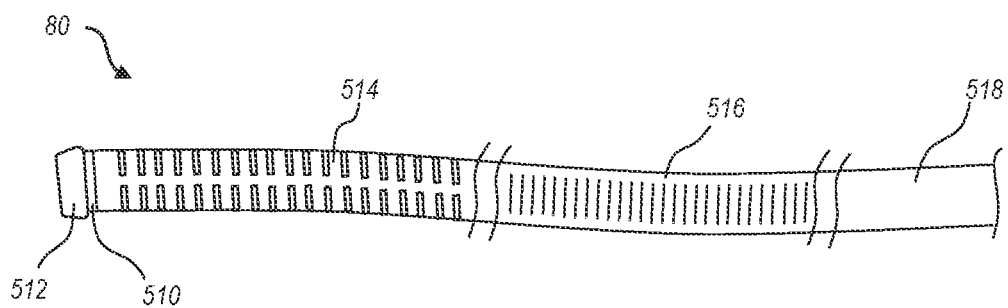
FIG. 11 illustrates the steering catheter, showing various features and sections that may be formed in the steering catheter.

FIG. 11 illustrates one embodiment of the steering catheter 80 in greater detail. In the illustrated embodiments, the steering catheter 80 includes a proximal section 518, intermediate section 516, and a distal section 514. A steering ring 510 (also referred to herein as a tip ring) is connected at the distal end. The one or more tension cables, described above, may extend through the steering catheter 80 and engage with or attach to the steering ring 510 to provide manipulation and control of the curvature of the steering catheter 80. A distal cap 512 positioned over the steering ring 510 or integrally formed with the steering ring 510 provides an angled/rounded surface that allows the steering catheter 80 to more effectively move and slide against the outer sheath 82 without binding. In this embodiment, the steering catheter 80 is formed as a hypotube, such as a laser cut hypotube. The proximal section 518 may remain uncut, while the intermediate section 516 and distal section 514 may be cut (e.g., laser cut) to increase flexibility. Although not shown in this view, a polymer layer may surround the steering catheter and forms an outer layer.

Additional details and embodiments related to the steering catheter 80 are described below in the sections titled "Detachment Mechanism for Steering Catheter from Steering Box", and "Reducing Friction between Steering Catheter and Outer Sheath."

In some embodiments, the steering catheter 80 is rotationally keyed to the outer sheath 82. The outer sheath 82 may include cut patterns and/or other features which are arranged to provide particular preferred bending directions.

In this embodiment, because bending of the outer sheath 82 depends upon curving of the steering catheter 80, rotational alignment of the outer sheath 82 to the steering catheter 80 is beneficial. These components may be keyed together using a key and corresponding keyway feature, slots and corresponding tabs, or other rotational keying mechanism known in the art. Alternatively, or additionally, alignment markers can be provided at the handle assembly to visually indicate alignment.

To provide effective steering and positioning at the mitral annulus, the distal section 514 is cut with a pattern which allows a bending radius of about 15 mm or less (e.g., 5 to 15 mm). The intermediate section 516 is cut to allow a bending radius of about 30 to 45 cm. The proximal section is uncut to provide the steering catheter 80 with sufficient stiffness, torquability, and pushability.

Figure 12:
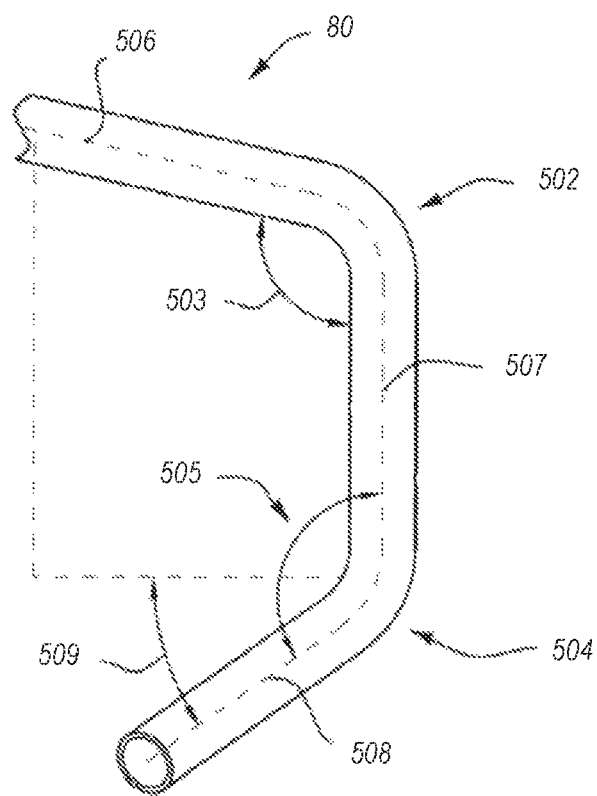
FIG. 12 illustrates the steering catheter after forming a compound curve shape to enable proper positioning of the delivery member relative to the mitral annulus.

FIG. 12 illustrates an example of a series of compound bends that the steering catheter 80 may perform during the delivery, repair, recapture, or repositioning of the IV device. While accessing the mitral annulus, the steering catheter 80 may be steered in at least two planes of motion. The two planes of motion may be substantially perpendicular to one another. The steering catheter 80 has a first bend 502 with a first bend angle 503 measured between a first longitudinal axis 506 and a second longitudinal axis 507. In some embodiments, the first bend angle 503 may be in a range of about 40° to about 120°, more often about 90° to about 120°, or about 105°. A second bend 504 is formed between a third longitudinal axis 508 and the second longitudinal axis 507. The second bend 504 may also have a rotational angle 509 relative to a plane in which the first longitudinal axis 506 and the second longitudinal axis 507 lie. In other words, the rotational angle 509 is relative to the amount of rotation of the third longitudinal axis 508 relative to the direction of the first bend 502. In one embodiment, the second bend angle 505 is in a range of about 45° to 135° or about 60°.

Figure 13A:
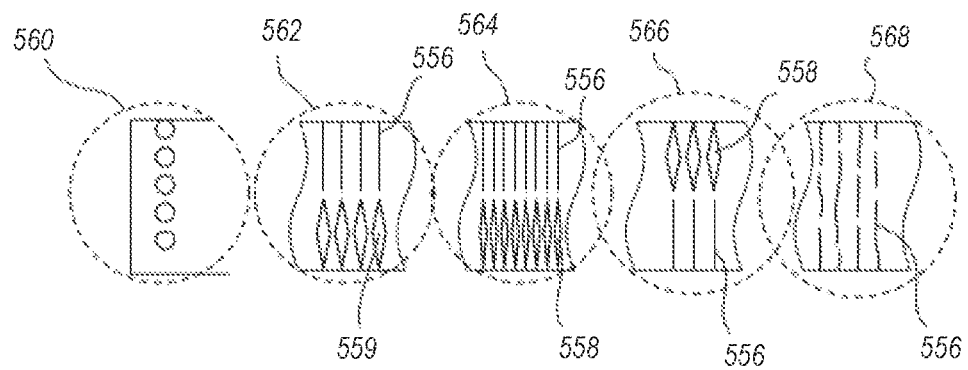
FIG. 13A illustrates various cut patterns which may be utilized in the outer sheath, steering catheter, or delivery catheter, including the can structure, to provide flexibility and/or preferential bending.
Figure 13B:
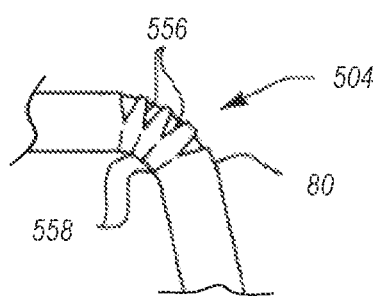
FIG. 13B illustrates bending of the steering catheter, showing features of the cut patterns which enable the bending.

FIG. 13A shows various cutting patterns that can be used in different sections of the steering catheter 80 (and corresponding sections of the outer sheath 82) to produce the desired bends. Each section can include cut patterns that can include one or more slits 556 and/or one or more island cuts 558. The slits 556 may transmit longitudinal force along the catheter and also allow expansion of the catheter when it is deflected in a direction opposite the slit 556. The island cuts 558 may allow compression of the catheter when it is deflected in a direction of the island cuts 558. For example, slits 556 and island cuts 558, when located on opposite sides from one another, may direct preferential bending of the catheter, as shown by exemplary bend 504 in FIG. 13B.

In one embodiment, illustrated in FIG. 13A, a cutting pattern can include five sections or regions 560, 562, 564, 566 and 568, with different cut patterns in each section. Such sections may be arranged as needed to provide the desired compound curve profile. For example, a first section 560 can include a plurality of holes radially spaced about the periphery of the catheter. A second section 562 provides for bending in a first direction, a third section 564 is similar to the second section 562 but with smaller sized and more closely spaced island cuts 558, a fourth section 564 provides for bending in a second direction, and a fifth section 566 includes multiple slits for adding flexibility without forming a particular bending direction. While the island cuts 558 are depicted as diamond-shaped, the island cuts 558 may have one or more other shapes, such as square, rhombohedral, triangular, rectangular, circular, oblong, other elliptical, other polygonal, irregular, or combinations thereof.

Additional details and embodiments related to the steering catheter 80, including additional and/or alternative cut patterns that may be utilized in the steering catheter 80, are described below in the section titled "Flexible Catheter Segment Capable of High Tensile Forces" and are also shown in part by FIG. 29.

Figure 14:
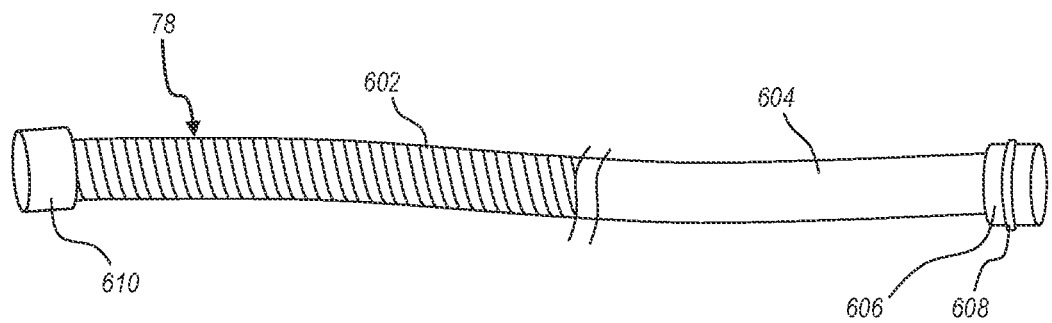
FIG. 14 illustrates a delivery catheter with distal cap structure configured for maintaining at least a portion of the IV device in a compressed configuration pre-deployment.

FIG. 14 illustrates one embodiment of the delivery catheter 78. The delivery catheter 78 includes a proximal section 604 and a distal section 602. At the proximal end, the delivery catheter 78 may include a seal 606 and an O-ring 608 for forming a fluid tight seal at the handle assembly 130, in particular at the delivery catheter holder 136. In the illustrated embodiment, the distal section 602 is formed as a coil. The coil provides the delivery catheter 78 with ability to effectively push the IV device through the steering catheter 80 as part of deploying the IV device. The coil also provides good flexibility for navigating a patient's tortuous vasculature.

The delivery catheter 78 also includes a can structure 610 disposed at the distal end. The can 610 is configured to constrain and hold at least a proximal section of a collapsible/expandable IV device 10. Without such constraint, the outer portion of the device 10 may bias radially outward against the inner surface of the overlying components of the delivery member 70, making it more difficult to unsheathe or re-sheathe the device 10. Further, in implementations where the IV device 10 includes hooks or barbs, the can 610 can aid in isolating the hooks/barbs and preventing them from catching onto cuts or other areas of the delivery member 70.

The can 610 may also have a length sufficient to aid in maintaining coaxial alignment of the distal end of the delivery catheter 78 within the delivery member 70 to avoid or minimize unwanted tilting. For example, the can 610 preferably has a length to diameter ratio of greater than or equal to 1, though in alternative embodiments the ratio may be smaller, such as about 0.25 to 1, depending on the stiffness of the distal section 602. The can 610 also provides an effective structural surface to act as a counterforce to maintain the IV device 10 in the proper pre-deployed position when the outer member is retracted. In some embodiments, one or more edge portions of the can 610 include a taper and/or smooth surface for easier sliding of the can 610 within the outer member.

Additional details and embodiments related to the delivery catheter 78, including additional and/or alternative can structure embodiments and additional or alternative structures for forming the structure of the catheter 78, are described below in the section titled "Echo Visualization of the Delivery Catheter Can" and are also shown in part by FIGS. 19, 20A and 20B.

Figure 15A:
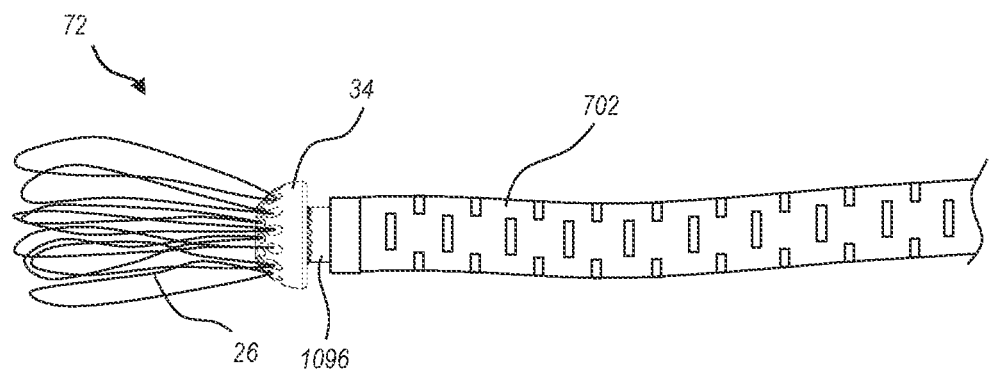
FIG. 15A illustrates an exemplary suture catheter that may be disposed within the delivery catheter of FIG. 14 and which is configured for controlling axial tension on the replacement heart valve.

FIG. 15A is a detailed view of the inner catheter 72 (which may also be referred to herein as a "suture catheter"). The inner catheter 72 may be utilized as part of the delivery member 70 to maintain axial tension of the IV device prior to deployment, and by so doing may aid in maintaining at least the proximal section of the IV device within the can 610. For example, the inner catheter 72 may include a connecting ring 34 with a series of suture loops 26 that may be tethered to corresponding attachment points of the IV device (see further details in FIGS. 16A through 16F). Retraction of the inner catheter 72 relative to the delivery catheter 78 adds axial tension to the IV device to maintain it in a pre-deployed position while distal movement of the inner catheter 72 relative to the delivery catheter 78 releases axial tension and allows deployment of the device.

Figure 15B:
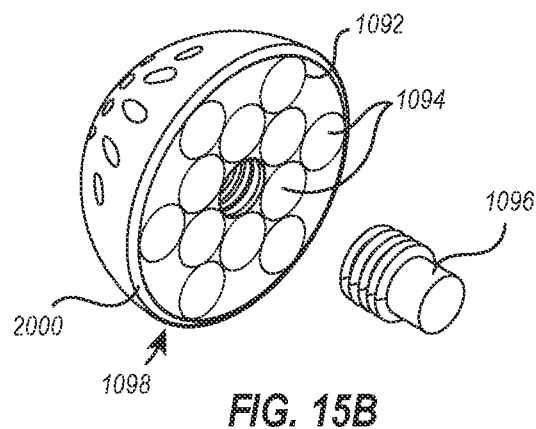
FIGS. 15B and 15C illustrates an alternative two-part embodiment of the suture catheter connecting ring of FIG. 15A.
Figure 15C:
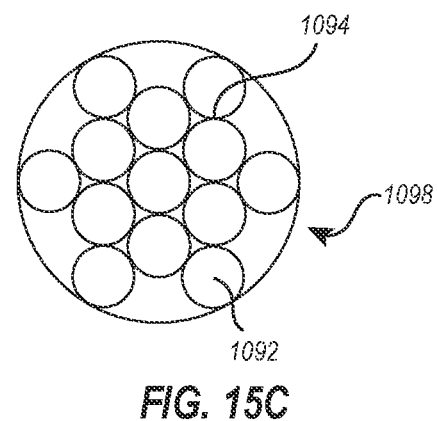

FIGS. 15B and 15C illustrate an embodiment of a two-part suture ring or connecting ring 34. A two-part suture ring 34 may allow for machining of the proximal end 1090 which is more difficult to achieve when the connecting ring 34 is formed as a single piece. When the proximal end 1090 of the connecting ring 34 is flat, the overlapping edges of the suture openings 1094 can result in sharp edges capable of wearing and damaging suture loops fixed within the openings 1094. To avoid damage to the suture loops 26, the proximal end 1090 can include smoothed and chamfered edges 1092 for the suture openings 1094 in order to avoid damage to the suture at the proximal end 1090 of the connecting ring 34. Particularly, in areas where the suture openings 1094 share an edge, the formed edge can be relatively sharp and cause damage to the suture thread. By chamfering and smoothing the suture openings 1094, this prevents wear and damage to the suture loops 26. The chamfering or smoothing should preferably be provided on both the distal and proximal ends of the suture openings 1094.

The connecting ring 34 can be comprised of two parts: a disk 1098 and a stem 1096. The disk 1098 can comprise the proximal end 1090 of the connecting ring 34 and can include suture openings 1092 with smoothed and chamfered edges 1092. When the connecting ring 34 is formed as a single piece, it may be difficult to use a laser or other device to chamfer and smooth the edges 1092, particularly on the proximal side of the suture openings 1094. This embodiment provides a mode for enabling a chamfer 1092 on the proximal face of the connecting ring 34 by providing for the disk 1098 to be machined first to add the chamfer and smoothing to the edges 1092 of the suture openings 1094. Next, the stem 1096 can be welded on to the proximal end of the disk by use of a laser.

Deployment of the IV Device

Figure 16A:
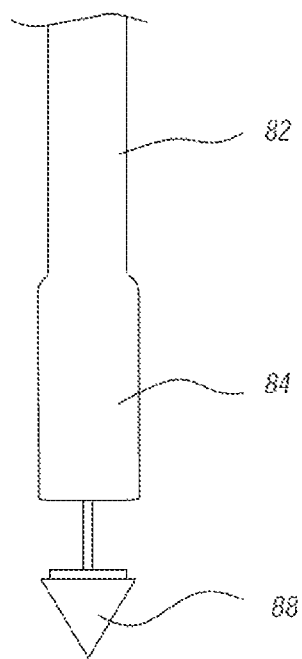
FIGS. 16A to 16F illustrate deployment and release of the replacement heart valve at the mitral annulus.
Figure 16B:
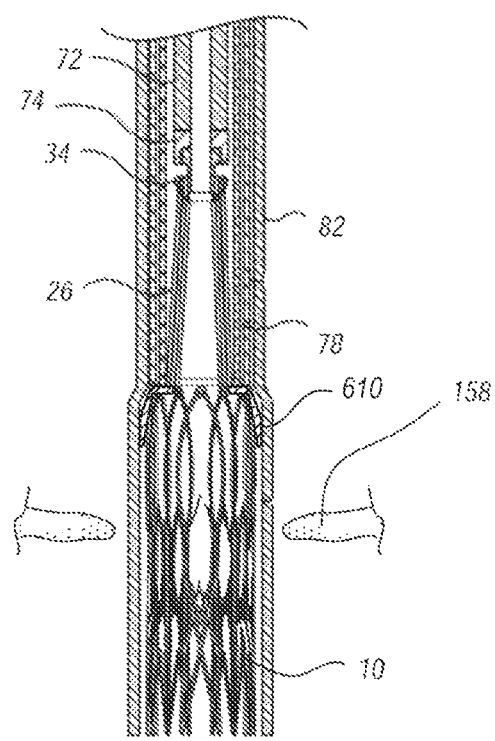
Figure 16C:
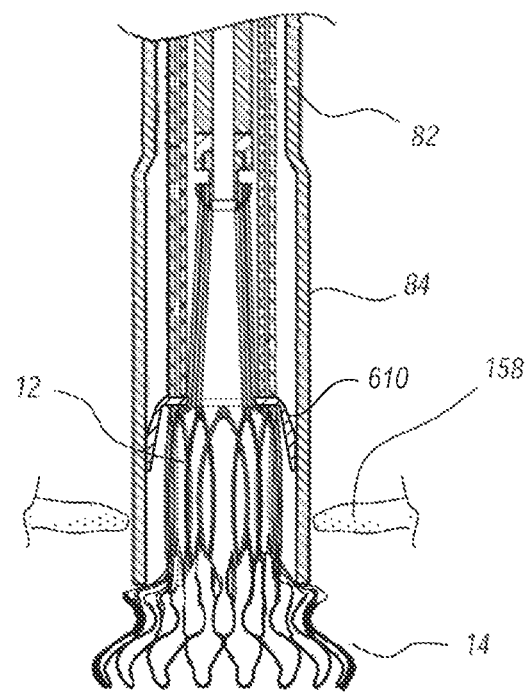
Figure 16D:
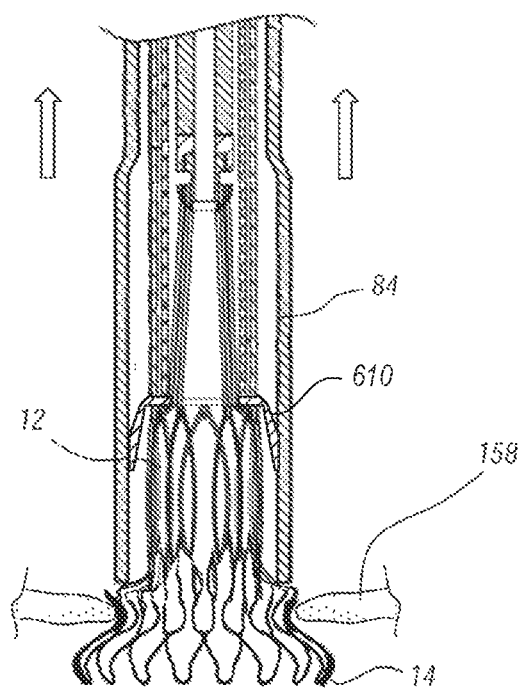

FIGS. 16A through 16F schematically illustrate deployment and release of an IV device 10 (shown here as an artificial, replacement valve) at the mitral annulus 158. As shown in FIG. 16A, the distal tip 88 is first advanced relative to the outer sheath 82 and valve cover 84 to provide sufficient space for deployment. For clarity, in following Figures, the tip 88 is not shown. FIG. 16B shows in cross-section the delivery member in position at the mitral annulus 158, with a distal portion of the artificial valve 10 positioned on the ventricular side, and a proximal portion of the artificial valve 10 positioned on the atrial side. Partial retraction of the outer sheath 82, as shown in FIG. 16C, allows the ventricular anchor 14 to release and expand. As shown in FIG. 16D, the artificial valve 10 may then be retracted proximally to bring the ventricular anchor 14 into contract against the mitral annulus 158. This may be accomplished by retracting the delivery catheter 78. Alternatively, the entire delivery member 70 may be retracted.

Figure 16E:
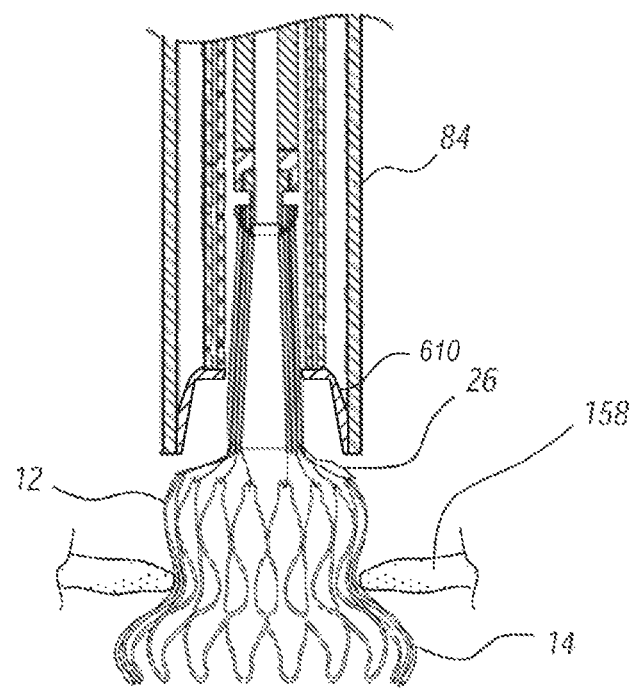
Figure 16F:
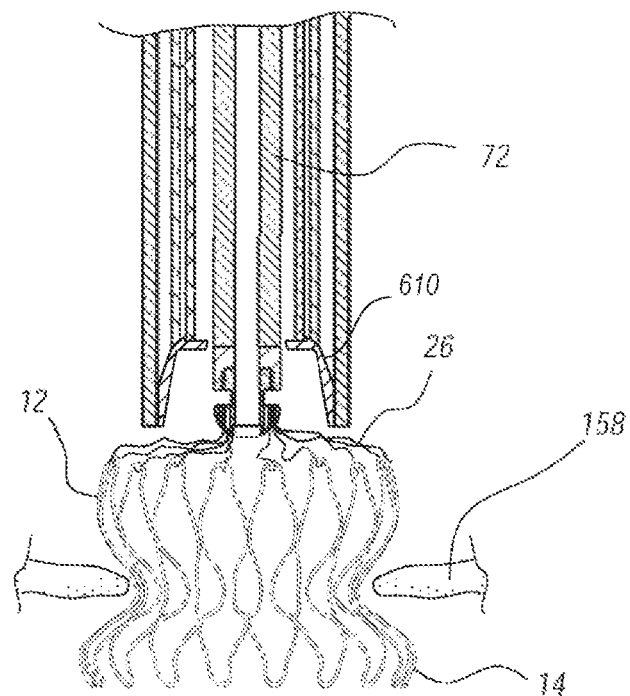

As shown by FIG. 16E, the valve cover 84 may then be further retracted to release the atrial anchor 12 on the atrial side of the mitral annulus 158. At this point, the replacement valve 10 may still held by the suture loops 26 in a position not yet fully deployed. This allows the replacement valve 10 to be further positioned or recaptured if necessary. As shown in FIG. 16F, the suture catheter 72 may then be distally advanced to relieve tension in the suture loops 26, allowing the atrial anchor 12 to more fully expand and release from the can structure. Even further distal advancement of the delivery catheter detaches the suture loops 26 and allows the delivery member 70 to be removed from the patient. The longitudinal position of the tip 88 relative to the suture catheter 72 can be adjusted as needed while the suture catheter 72 is advanced. After the replacement valve 10 is detached, the tip 88 is retracted and reconnected to the valve cover 84 prior to removal of the delivery member from the patient.

Prior to deploying the IV device, it is necessary to position the distal end of the delivery system, particularly the valve cover with the collapsed IV device contained therein, relative to the target site of the patient's anatomy with a relatively high degree of accuracy. For example, in the case where the IV device is a replacement mitral valve as graphically illustrated in FIGS. 16B, prior to beginning deployment of the artificial valve, the delivery system is first manipulated to position the valve cover 84 within the mitral annulus 158 as shown in FIG. 16B. To assist in visualization during positioning and deployment, echogenic and/or radiographic markers can be provided at various locations and/or on various components of the delivery system as discussed below.

Echo Visualization of the Valve Cover

As discussed above, the valve cover 84 functions to house an IV device in a compressed, pre-deployed state during intravascular delivery of the device to the targeted cardiac site. During delivery of the device, echo visualization of the valve cover 84 and distal tip 88 are advantageous for the delivery of the artificial valve to the mitral annulus. In some cases, however, the valve cover can be made from a non-radiopaque or low-density material. In such cases, it can be useful to make a groove in the outer sheath to use as a guideline under fluoroscopy or echocardiogram to help the surgeon in positioning the device. Turning to FIG. 17, for example, echo markers 710a can be located at various positions along the length of valve cover 84. In some embodiments, one or more echo markers 710a can be positioned along a middle section 704 of a valve cover 84. The middle section 704, as shown in FIG. 17, is the area between the distal end 706 and the proximal end 708 of the valve cover 84. In one embodiment, the echo marker 710a can be positioned at a location which is approximately in-line with the waist of the artificial valve 10 when it is in its collapsed state and housed within the valve cover 84. In any such case, echo marker can be provided by forming an annular groove in the outer surface of the valve cover 84 and placing a layer of echogenic or radiopaque material within the groove. The valve cover 84 may also include an outer jacket 712 (sometimes referred to as outer sheath 712) surrounding the exterior of the valve cover 84. The outer jacket 712 may comprise a flexible material, such as thermoplastic polyurethane, for example, Texin® aromatic polyether-based thermoplastic polyurethane (TPU).

Figure 18A:
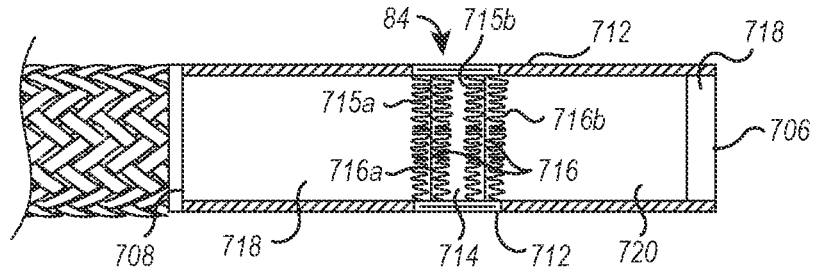
FIGS. 18A to 18D illustrate additional embodiments of a guide line or echo marker on a valve cover for echo visualization of the delivery device during a delivery procedure.

FIGS. 18A-18D illustrate an alternative embodiment of a guide line or echo marker for echo visualization of the delivery device during a delivery procedure. As shown in FIG. 18A, a valve cover 84 is covered with an outer jacket 712 comprising a flexible material such as those described above. In some embodiments, at least one or more portions of the valve cover 84 can include laser cut surfaces 720 to impart the valve cover 84 with the ability to bend. A valve cover 84 can include a combination of laser cut surfaces 720 and non-laser cut surfaces 718. One or more glue fillets 716 are applied to the groove. A first glue fillet 716a is applied to a proximal end 715a of the groove 714, and a second glue fillet 716b is applied to a distal end 715b of the groove 714. In this configuration, the glue fillets 716 can create a full seal around the groove 714, thereby trapping air within the groove 714 under the outer jacket 712. The trapped air can be visible under echocardiogram.

Figure 18B:
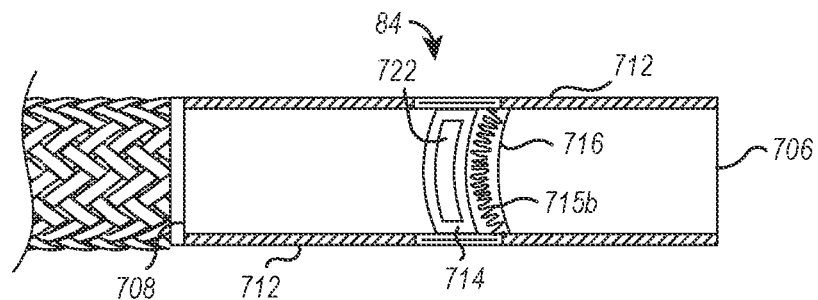

FIG. 18B illustrates a valve cover 84 having a groove 714 forming an annular ring or indentation surrounding a portion of the exterior of the valve cover 84. A piece of heat shrink 722, such as polyethylene terephthalate (PET) or fluorinated ethylene propylene (FEP), can be applied to the groove 714 and shrunk in place on to the groove 714. An outer jacket 712 can then be applied to cover the exterior of the valve cover 84 as well as the heat shrink 722 applied within the groove 714. A glue filet 716 can then be applied to a distal end of the valve cover 84. This configuration allows the glue fillet 716 to form a bond and full seal around the outer jacket 712, thereby trapping air under the heat shrink 722, rendering the trapped air visible under echocardiogram.

Figure 18C:
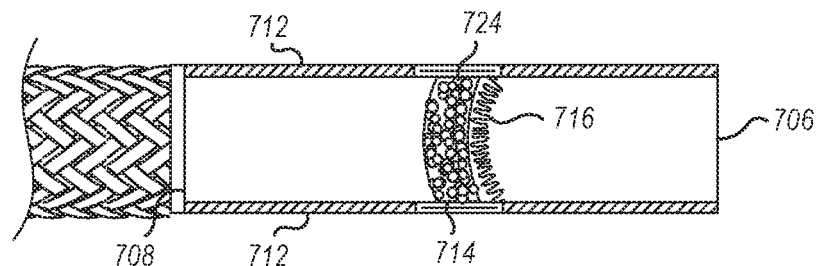

FIG. 18C illustrates a valve cover 84 having a groove 714 forming an annular ring or indentation surrounding a portion of the exterior of the valve cover 84. Microspheres 724 can be mixed with glue and applied to the groove 714. An outer jacket can then be applied to cover the exterior of the valve cover 84, and a glue fillet 716 can be applied to the distal end of the valve cover 84. The glue filet 716 creates a bond and full seal around the outer jacket 712. The microspheres 724 sealed within the groove 714 are visible under echocardiogram.

Figure 18D:
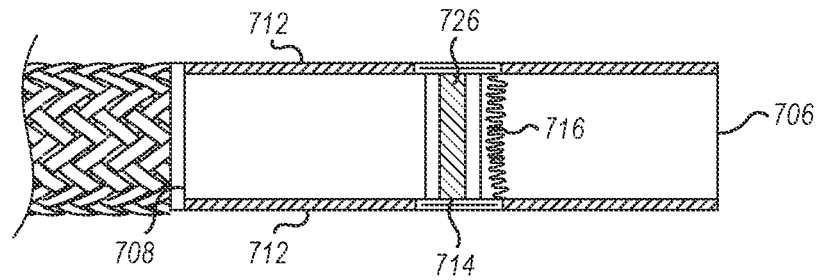

FIG. 18D illustrates an alternative application for a groove 714 of a valve cover 84 in order to render the valve cover 84 visible under fluoroscopy. A radiopaque material 726 can be applied to the groove 714 of a valve cover. An outer jacket can then be applied to cover the exterior of the valve cover 84, and a glue fillet 716 can be applied to the distal end of the valve cover 84. The glue filet 716 creates a bond and full seal around the outer jacket 712. The radiopaque material 726 is visible under fluoroscopy in order to facilitate the correct placement of a device during a delivery procedure. The radiopaque material 726 can comprise materials such as tungsten, tantalum, gold, platinum, iridium, barium sulfate, or the like.

Echogenic Attachable Distal Ring

Figure 21A:
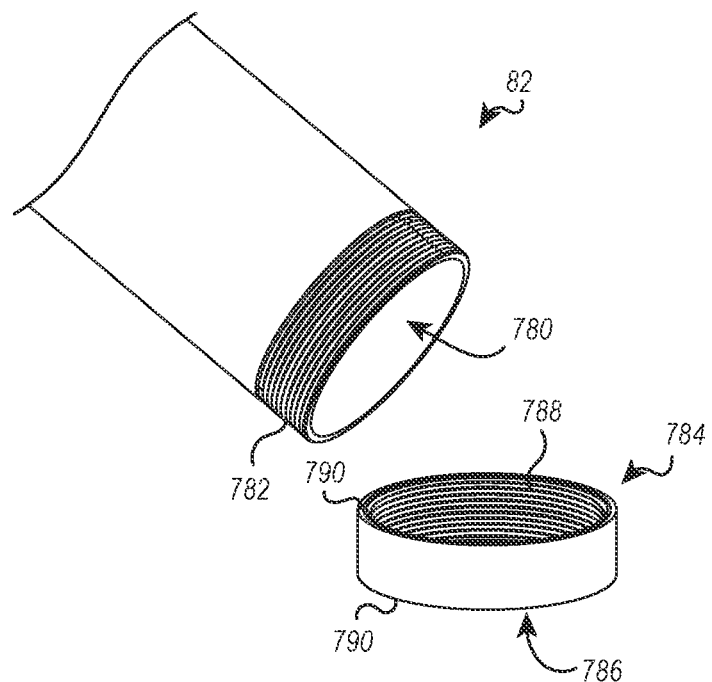
FIG. 21A illustrates an embodiment of a radiopaque distal ring configured to be attached of the distal end of the valve cover.
Figure 21B:
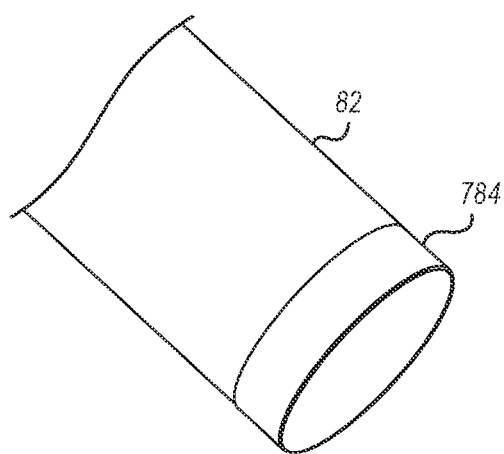
FIG. 21B illustrates an assembled valve cover with radiopaque distal ring.

FIGS. 21A and 21B illustrate another embodiment of a radiopaque marker that can be provided on the valve cover 82. In this embodiment, valve cover 82 can be made to include a threaded portion 782 at its distal end 780. The distal ring 784 can comprise a thin-walled tube having internal threads 788 compatible with the external threaded portion 782 of the outer sheath 82. Distal ring 784 can be formed of materials rendering it visible under fluoroscopy, such as radiopaque materials, for example, stainless steel, tungsten, platinum iridium, or the like. When the distal ring 784 is assembled on the distal end of an outer sheath 82, as shown in FIG. 21B, the distal ring 784 can provide an echogenic locating feature for the position of the distal end of the delivery system. The distal ring 784 can also include an atraumatic outer profile 786 for safe delivery of the device to provide a smooth transition between the distal end of valve cover 82 and atraumatic distal tip 88. The outer profile 786 of the distal ring 784 can have rounded edges 790 on both ends of the distal ring 784, providing atraumatic edges on either side, thereby enabling threading of the distal ring 784 from either side.

Echo Visualization of the Delivery Catheter Can

As described above, it may be advantageous for the delivery catheter 78 to be visible to physicians during delivery of a device. The can 610 sits within the valve cover 84 and holds the replacement valve and helps to control deployment of the replacement valve. Thus, when the IV device 10 is positioned within valve cover 82 in a crimped or collapsed state prior to placement and/or deployment, the can 610 is located adjacent the proximal end of the IV device (and, more particularly, adjacent to the proximal end of the atrial anchor 12 of the IV device 10). In some embodiments, the can 610 can include one or more radiopaque markers to cause the can 610 to be visible under fluoroscopy during a procedure. For example, FIG. 19 illustrates a can 610 having an radiopaque marker in the form of an radiopaque ring 728 which is placed around the circumferential surface of the can 610. This better helps track the location of the IV device during surgery and also helps identify the sequential phases of the deployment of the valve. This can improve control and knowledge of the procedure in real-time, positively impacting patient safety and surgery time.

The can 610 can include a groove 736 spanning the circumferential surface of the can 610. The groove 736 can be sized to receive an radiopaque ring 728. In some embodiments, the groove 736 can be inset within the surface of the can 610 so that the groove edges 735 terminate at the surface of the can 610, while in other embodiments, the edges 735 can protrude outward from the surface of the can 610 thereby providing increased support to the radiopaque ring 728 situated within the groove 736.

The groove 736 can serve as an indicator of an initial taper point 737 at which the proximal surface 734 of the can 610 begins to taper or narrow towards a distal end 732 of the can. The distal surface 731 of the can 610, situated on the opposite side of the groove 736, can extend towards a proximal end 730 of the can 610 and can maintain a level surface, as shown in FIG. 19.

Radiopaque ring 728 can be comprised of one or more radiopaque materials visible under fluoroscopy, such as various metals. For example, the radiopaque ring 728 may comprise materials such as tungsten, tantalum, gold, platinum, iridium, barium sulfate, or the like.

Echo Visualization of Atraumatic Distal Tip

In yet another embodiment, one or more additional echogenic and/or radiopaque markers can also be provided on the atraumatic distal tip 88, which is used to close the distal end of the valve cover 84 during advancement of the delivery member through a patient's vasculature and positioning of the device at the targeted anatomical site. As discussed above, when distal tip 88 is positioned against the distal end of valve cover 84, the proximal end of distal tip 88 is positioned adjacent the distal end of the IV device (and, more particularly, adjacent the distal end of the ventricular anchor 14 of IV device 10). Thus, with the various markers discussed herein, the position of the IV device, such as a replacement mitral valve, relative to the targeted anatomical site can be tracked with a relatively high degree of precision.

With many medical devices, including temporarily or permanently implanted devices, it is usually necessary to reduce the system or devices profile. Even if a radio opaque marker can be made relatively thin, it nevertheless could increase the profile of the system or device if placed on an outside diameter. As an example, if a radiopaque marker is placed on the outside of an outer sleeve, it will increase the diameter. Similarly, if it is placed on the inside of the outer sleeve it might interfere with the intravascular device contained therein, when the outer sleeve is moved relative to the intravascular device, such as being pulled back or pushed forward. Placing a marker on the shaft might position it to far distal the distal end or the intravascular device. A marker on a distal end of the structure used to advance the intravascular device might be difficult to see, depending on the material forming the marker.

Based upon this, in some configurations, a marker placed in a cap or end of the catheter might be desirable. A tip, such as the distal cap described herein, is typically made from a soft polymer, Silicon or rubber to allow an atraumatic navigation through the anatomy of the patient. Furthermore, the tip or distal cap could be made of a foamy material to allow visualization under echocardiography guidance. Lastly to allow a ghost like image of the tip or distal cap under x-ray, for instance, a contrast agent like barium sulfate could be added.

Figure 22:
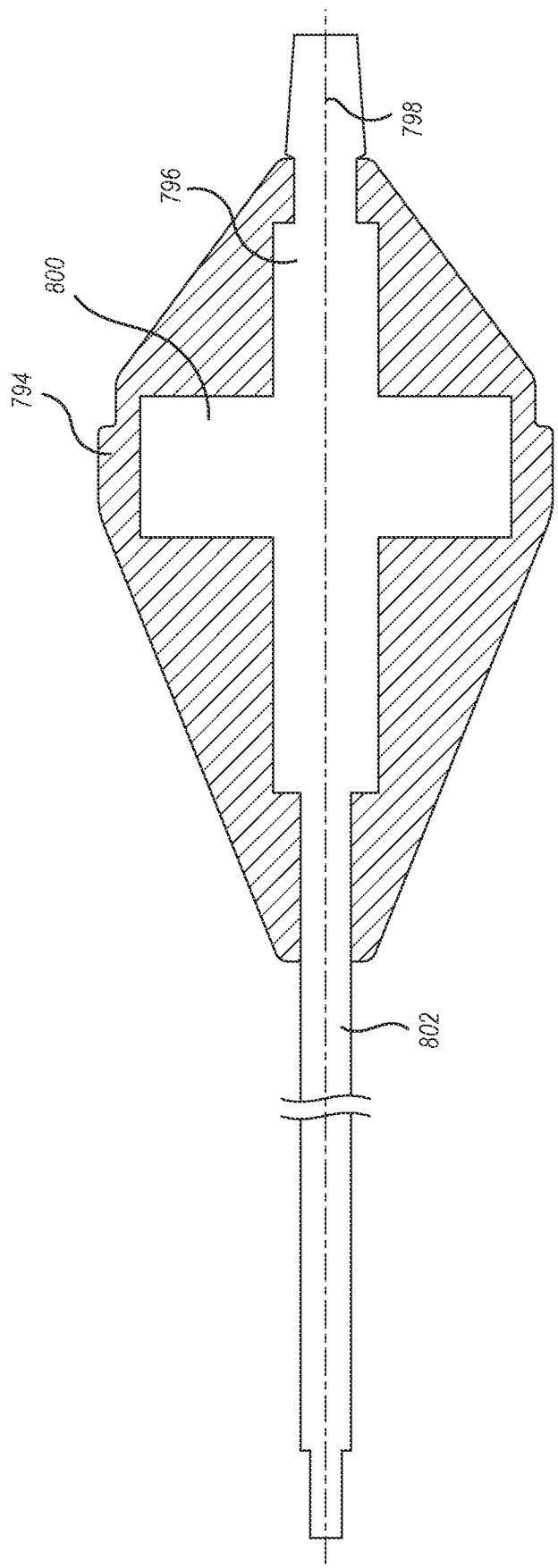
FIG. 22 illustrates an alternate embodiment of an atraumatic distal tip of the delivery system with embedded radiopaque and/or echogenic markers.

As illustrated in FIG. 22, in the described configuration, the marker is embedded in the tip or distal cap 794 of the catheter and is perpendicular to a longitudinal axis 798 of the tip or distal cap 794. The tip or distal cap 794 is connected to a guidewire receiving member 796 and this connection is strong to avoid the tip or distal cap 794 being sheared of the guidewire receiving member 796 in the human body. A simple over-mold or gluing of the tip or distal cap 794 to the guidewire receiving member 796 might be difficult, depending on the material choice of the guidewire receiving member and the material of the tip or distal cap.

To overcome this potential difficulty, the tip or distal cap is secured to the guidewire receiving member through a mechanical interaction. In one configuration, the tip or distal cap 794 is molded over an insert 800 attached to the guidewire receiving member 796.

An insert 800, typically produced in a separate step, will be attached to the guidewire receiving member 796. The insert can be machined, injection molded, manufactured using additive manufacturing, combinations thereof, or other manufacturing techniques. The insert can be made from a variety of different materials including, but not limited to, polymers, metal, ceramics, composites, alloys, etc. Material for an insert, in some configurations, could be Polycarbonate or Nylon since these materials can be injection molded and can be easily glued with variety of different adhesives.

Figure 23A:
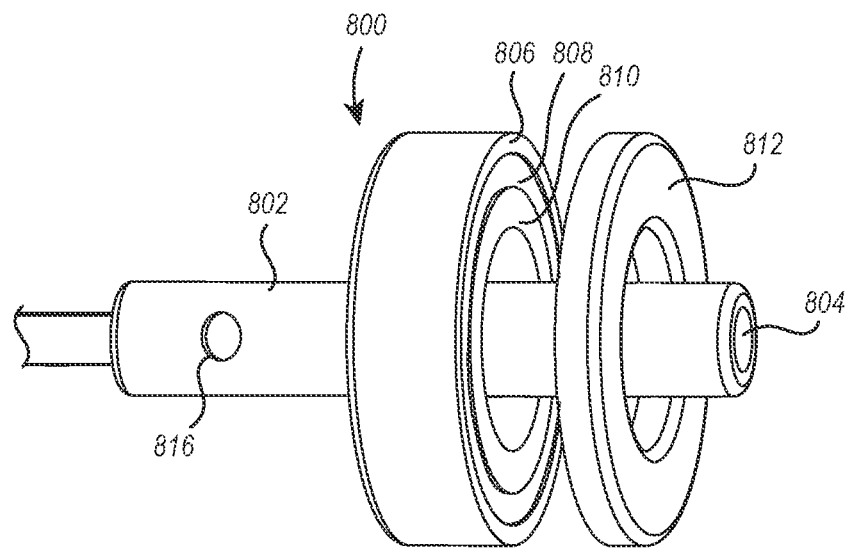
FIGS. 23A-23B illustrate an alternate embodiment of an atraumatic distal tip of the delivery system with embedded radiopaque and/or echogenic markers.
Figure 23B:
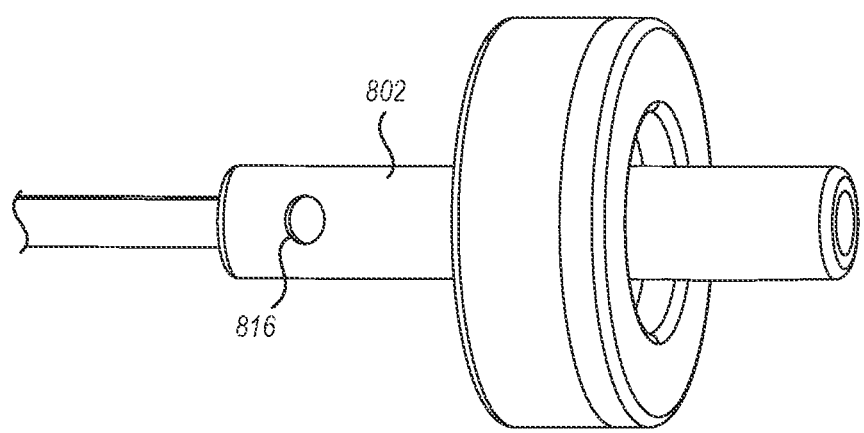

As illustrated in FIG. 23A-23B, the insert 800 includes an elongate member 802 having a lumen 804 configured to receive the guidewire receiving member. Separated from the elongate member is a rim member 806 having a groove 808 configured to receive a marker band, wire, or other elongate structure. The marker 810 can be received within the groove 808, and optionally can include an elongate end that is mounted through a base of the groove and into the body of the insert 800. Alternatively, instead of a single groove, the rim member can include a plurality of recess, with each recess receiving a radio opaque or radiopaque marker. The combination of those recess and markers approximating a ring. In still another configuration, the groove can include a plurality of recess with the band, ring, etc. extending across the recesses and those recesses optionally filled with additional radio opaque or radiopaque material, or some other material.

In some embodiments, the elongate member includes a port through which glue or an adhesive can be injected to aid with bonding or connecting the insert to the guidewire receiving member. Various glues or adhesives are know to those skilled in the art, including, but not limited to UV and non-UV curable adhesives.

In other configurations, whether in addition to or instead of using adhesives, the elongate member 802 includes a plurality of mechanical engagement structures 816 to interference or friction fits with the outside of the guidewire receiving members 796. For instance, complementary detents or other engaging structures 816 allow the insert to be securely attached to the guidewire receiving member before molding.

After the insert 800 has been connected to the guidewire receiving member 796, the radio opaque or radiopaque marker 810 is placed in the groove 808 of the insert 800, and optionally attached using adhesives or mechanical engagement. With the marker 810 in place, the guidewire receiving member 796 with the insert 800 attached, is placed into a mold and over-molded with the distal cap 794, such as a polymer described above. The open structure of the insert attached to the guidewire receiving member allows for a strong mechanical interaction of the tip or distal cap with the insert. The groove in the insert allows the radio opaque or radiopaque marker to be positioned perpendicularly to the axis of the guidewire receiving member.

Figure 24:
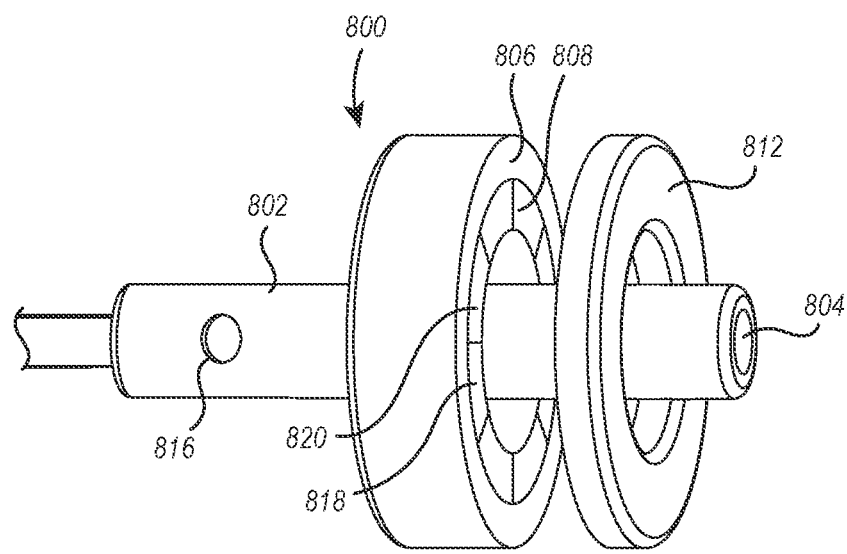
FIG. 24 illustrates an alternate embodiment of an atraumatic distal tip of the delivery system with embedded radiopaque and/or echogenic markers.
Figure 25:
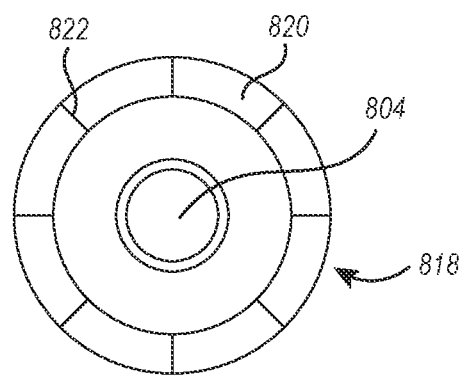
FIG. 25 illustrates a front end view of an insert for an atraumatic distal tip of the delivery system.

In some embodiments, the insert 800 can include an echogenic marker providing visualization of the device under ultrasound. An echogenic marker can consist of air being deliberately trapped in a designated space, such as within a cavity of an interior wall of an insert. FIG. 24 illustrates an embodiment of an echogenic marker 818 comprising a series of air pockets 820 organized in a concentric ring within the groove 808. FIG. 25 illustrates a front end view of the insert 800 with an echogenic marker 818. In some embodiments, the echogenic marker 818 can be used instead of a radiopaque marker 810. In other embodiments, the radiopaque marker 810 and echogenic marker 818 may be used simultaneously or incorporated into the same marker. For example, the segments 822 defining the air pockets 820 of the echogenic marker 818 can comprise radiopaque materials. For example, the segments 822 can comprise tantalum. The combination of an echogenic marker 818 with radiopaque materials can allow the device to be visible under both x-ray and ultrasound.

One or more of the distal cap embodiments described herein may be utilized in an interventional cardiac procedure. One exemplary embodiment includes the steps of: positioning a radiopaque wire within the coronary sinus of a patient, the radiopaque wire enabling identification of a plane of the mitral annulus; operating an intravascular device delivery system to cause a distal cap to extend through the mitral annulus, the distal cap including a radiopaque marker band at least partially formed in a ring structure; positioning the distal cap to bring the radiopaque marker band into planar alignment with the radiopaque wire, thereby bringing the distal cap into planar alignment with the plane of the mitral annulus. Embodiments may further include delivery of an intravascular device to the mitral annulus, deployment of an intravascular device at the mitral annulus, removal/retraction of the distal cap from the mitral annulus, and combinations thereof.

In one example, an imaging source (e.g., x-ray machine) is oriented such that the radiopaque wire positioned within the coronary sinus is substantially viewable as a line in the corresponding two-dimensional imaging. In other words, the imaging source is positioned such that the x-rays (or ultrasound or other source suitable for the particular imaging technique used) pass through the patient in a path substantially parallel to the plane of the mitral annulus. An operator may bring the distal cap into alignment with the mitral annulus by positioning the distal cap to cause the radiopaque marker band (e.g., ring structure) to also be visualized substantially as a line. In this manner, the more aligned the distal cap is to the mitral annulus, the more line-like the two-dimensional visualization of the radiopaque marker band will appear, and the less aligned the distal cap is to the mitral annulus, the less line-like (and more band-like or ring-like) the two-dimensional visualization of the radiopaque marker band will appear.

Hard Stop for Can

When loading an IV device, such as an artificial replacement heart valve, into the delivery system, it is important that the IV device be properly positioned within the valve cover and related components. Complications to the procedure can arise if the IV device is inserted to far into the delivery system (sometimes referred to as "overloading") or if the IV device is not loaded far enough into the delivery system (sometimes referred to as "underloading"). To assist in the proper positioning of the delivery catheter 78 relative to other components of the delivery system and thereby prevent "overloading" or "underloading," FIGS. 20A and 20B illustrate another embodiment of a distal ring 738 that may be utilized at the distal end of the steering catheter 80 (e.g., corresponding to steering ring 510 and distal cap 512 described above).

In this embodiment, the internal diameter of distal ring 738 can be sized to prevent the can 610 (when moving in a proximal direction) from passing beyond the distal ring 738. Distal ring 738 can comprise a body portion comprising a threaded section 746 and a stop ring 744. The threaded section 746 can comprise the proximal end 742 of the distal ring 738, and the stop ring 744 can comprise the distal end 740 of the distal ring 738. The stop ring 744 can have an outer rim 747 extending in an outward direction forming an over-hang or flange 748. The distal ring 738 can have an aperture 739 therethrough to allow a can 610, or at least a portion of a can 610, to fit within the aperture 739. The wall thickness of the distal ring 738 can be increased to disallow the can to pass beyond the distal ring 738, as illustrated in FIG. 20C. The distal ring 738 aperture 739 allows sufficient clearance for a device, such as a catheter, to pass through. The distal ring 738 can be made of metal or other radiopaque materials.

The distal ring 738 can be attached to the proximal end of a valve cover and the distal end of the outer sheath 82 of the delivery catheter. The distal ring 738, as described herein, can eliminate the need to visually confirm the ideal stop location of the can 610, or other device, which can eliminate user error. It can also prevent the can 610 from advancing too far into the delivery system and can eliminate the potential for damage to the delivery system or other device used with this procedure.

Valve Loading with a Balloon to Crimp

Another issue sometimes encountered with loading an IV device into the delivery system is non-uniform folding of the IV device as it is collapsed or crimped. It has been found useful to provide some form of internal support to the IV device during the crimping process. And, yet, after the IV device has been crimped, any such inner support feature most be capable of being removed in a manner that does not damage the leaflets or otherwise damage the structure of the collapsed IV device.

In some embodiments of the valve delivery system, the use of a balloon catheter 900 has been found useful in providing internal support to the IV device during the crimping process. A non-compliant balloon may be used as the inner support feature to allow for a rigid support structure during loading, which can then be depressurized, thereby reducing the outer diameter and making the surface of the balloon catheter compliant for removal from the delivery system.

The balloon catheter 900 as shown in FIG. 28, can comprise an outer hypotube 902, which interfaces with an inner hypotube 904. A balloon 906 can be configured to surround the point of interface between the inner hypotube 904 and outer hypotube 902. The distal end 907 of the balloon is mounted to the inner hypotube 904, which can be positioned over a guidewire or mandrel, passing out the proximal end of a y-connector 908. The balloon 906 can be created from a balloon material such as Nylon 12. The y-connector may have a luer lock connector 910. The balloon 906 can be mounted at a given distance that locates the balloon 906 to a feature on the delivery system which positions the balloon 906 for the crimped valve frame support. The proximal end 909 of the balloon is mounted to an outer hypotube 902 that is connected to a distal end of the y-connector 908, serving as the conduit to pressurize. When under high pressure, the balloon 906 becomes non-compliant during crimping and loading into the delivery system. When the pressure is released from the balloon catheter 900, the system can be removed from the crimped valve inside of the delivery system without comprising the integrity of the valve leaflets or stent structure.

Attachable Nosecone Catheter

With at least one prior embodiment of the delivery system described above, another issue that sometimes arose in relation to loading the IV device and assembling the delivery system was the fact that the atraumatic distal tip 88 (sometimes also referred to herein as the "nosecone") was permanently bonded to the distal end of the guidewire tube 86. This meant that, once the IV device was loaded into the valve cover, the guidewire tube 86 had to be "backloaded" into the delivery system from the distal end of the system, which could sometimes cause damage to the free edges of the IV device. Another issue present with one prior embodiment of the nosecone, was that the nosecone was either not visible under various imaging devices during the procedure, or that the nosecone was configured with a marker that was only visible under one imaging device, and not under another, thereby limiting a user's imaging options.

Figure 26A:
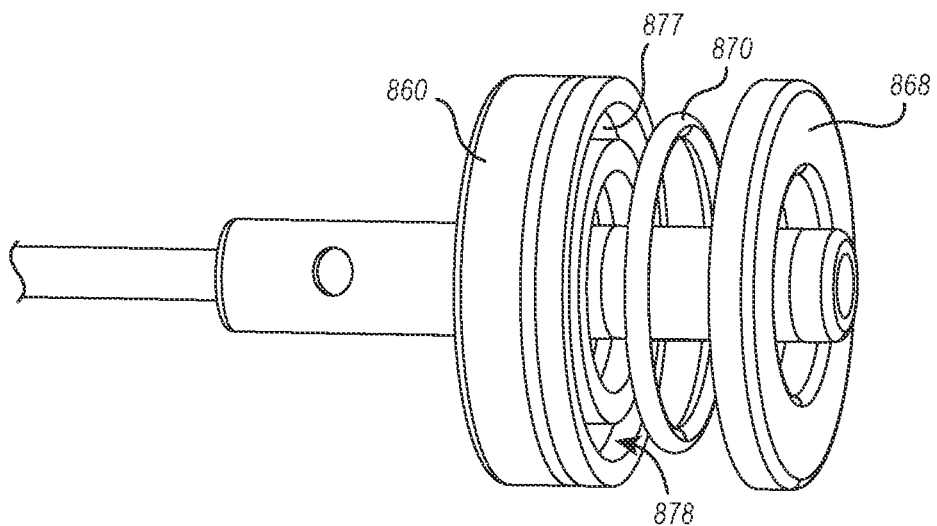
FIGS. 26A to 26B illustrate an alternate embodiment of an atraumatic distal tip of the delivery system with embedded radiopaque and/or echogenic markers.
Figure 26B:
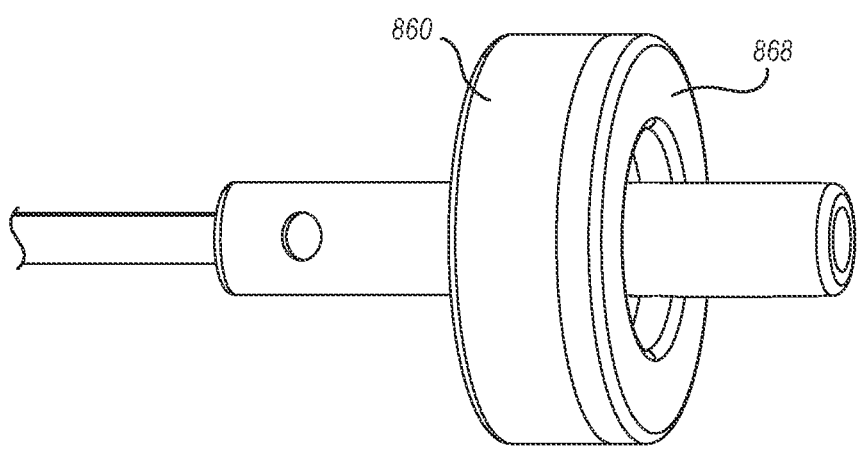

In an embodiment where the nosecone is enhanced with a dual marker system, the internal geometry of the nosecone can include echogenic traits. Echo is visible when there are void spaces, or air, produced by internal features. FIGS. 26A and 26B illustrate an embodiment of a dual marker system 880. The internal structure can include a circumferential void or enlarged groove 877 in which a radiopaque marker 870 is placed. The radiopaque marker can be made of any radiopaque material such as tantalum. The enlarged groove 877 includes extra space, in other words, the radiopaque marker does not fill the entire space of the groove 877, rather void space allows for air to be trapped within the groove 861 resulting in an echogenic marker 878. In some embodiments, the groove 877 can be filled with an MRI contrast solution, such as gadolinium, or any other material that is visible in Magnetic Resonance Imaging (MRI). Once the radiopaque marker is placed into the groove 877, the groove 877 is then sealed with a circumferential washer 868 and glue. This dual marker system 880 can then be over-molded onto a nosecone.

FIGS. 27A and 27B illustrate an alternate embodiment of the guidewire tube 86 and nosecone 88, which provides for selective attachment and detachment of nosecone 88 from guidewire tube 86. This also allows the guidewire tube 86 to be pre-loaded into the system prior to packaging and shipment and simplifies the process of setting up of the delivery system prior to a procedure, among other advantages.

FIGS. 27A and 27B illustrate an embodiment of an attachable nosecone catheter 850 that can be utilized at a distal end of the guidewire tube, such polyimide tube 852. The nosecone catheter 850 as described herein, can be attached and detached at the distal end of a polyimide tube 852. When fully assembled, the polyimide tube 852 can be inserted into the nosecone catheter 850 via the proximal lumen 854 as shown in FIG. 26A. The nosecone catheter 850 as shown in FIG. 27B, can have a proximal end having a proximal lumen 854 extending through the length of the nosecone catheter 850 to a distal lumen 856. The lumen 858 extending between the proximal lumen 854 and the distal lumen 856 can accommodate the positioning of the assembly 862. An interior portion of the lumen 858 can include a receiving structure 864 configured to receive an attachment element 872 of the hypotube 874.

The receiving structure 864 can be surrounded by an annular support 860, which can include a groove 861 for receiving an echogenic or radiopaque marker, such as a radiopaque ring 870. The radiopaque ring may be made of any radiopaque material such as tantalum. A washer 868 can be positioned against the groove 861 after the radiopaque ring 870 is inserted into the groove 861 in order to secure the ring 870 within the groove 861. In another embodiment, the nosecone can be enhanced to provide a dual marker system with both a radiopaque marker and an echo marker. Both markers can be on the same plane and can have similar geometry when viewed under fluoroscopy and ultrasound. This may allow surgeons to determine the location of the nosecone inside of various anatomical locations, such as within a beating heart while using both fluoroscopy and ultrasound. This may advantageously decrease surgery time, enhance reference geometry for devices such as a valve or a delivery system, thereby increasing patient safety.

Turning now to FIG. 27C, the assembly 862 may comprise a hypotube assembly and/or a polyimide tube assembly. In one embodiment, the selectively attachable feature of the nosecone catheter 850 can be achieved by a polyimide tube 852 assembled with a hypotube 874 on the distal end 876 of the polyimide tube 852. The hypotube 874 can comprise metal. The hypotube 874 can have a selective attachment element, such as threads 872 which can mate with a complementary receiving structure 864 to selectively secure the assembly 862 to the nosecone catheter 850 by inserting the assembly 862 into the proximal lumen 854 of the nosecone catheter 850. However, in other embodiments the selective attachment element may comprise snap-on or snap-in mechanisms, magnets, or the like which can mate with their counterpart receiving structure. The selective attachment element may be formed of organic, inorganic, ceramic, and/or metal materials.

Reducing Friction Between Delivery Catheter and Suture Catheter

As disclosed above, the delivery system comprises a plurality of individual elements or catheters, which are concentrically assembled within one another. Also, one or more of the individual catheter elements may comprise one or more sections that may be fashioned out of a hypotube having laser cuts to facility bending. Further still, in order to deliver a valve prosthesis (such as an artificial mitral valve prosthesis), the system requires that each of these catheters/layers be able to move independently of the other catheters/layers. This can be challenging if elements have to be moved inside of a laser cut hypotube when the hypotube is deflected with small bending radii in one or more planes. It is challenging to entirely smooth the interior edges of a laser cut hypotube. This is of particular concern when running a polyimide tube on the inside surface of a hypotube. If the inside surface of the hypotube is not smooth, there is potential for the polyimide tube to shave off small particles, which when shaved off, can be released into a patient's bloodstream, potentially resulting in a number of serious problems. Furthermore, the friction between a polyimide tube of one catheter/layer and a laser cut hypotube of an adjacent catheter/layer can be high (particularly, when the delivery member is deflected with small bending radii in one or more planes), making it more difficult to move the polyimide tube relative to the laser cut hypotube.

In order to reduce friction, a liner may be added on the inner side of the hypotube. The liner can be made from materials having a low friction coefficient such as PTFE, FEP or other Fluoropolymers. However, these materials do not bond easily to stainless steel. With corona treatment or etching it is possible to increase the ability to bond, however it is unlikely to be maintained on the inside surface of a tube which must undergo deflection caused by sharp bending radii. This would result in a high risk of delamination.

For example, in an alternate embodiment of the delivery catheter 78, a fluoropolymer tube, such as a PTFE tube 938, can be added along the bending portion of delivery catheter 78 to the inside of a laser cut hypotube 442 that makes up a portion of delivery catheter 78. Tube 938 can be held in place by small rings 932, 934 which can be welded to the hypotube 442. The rings may provide the fluoropolymer tube with an increased range of motion within the hypotube. The rings allow the PTFE tube 938 to "free flow" inside of the hypotube. A distal ring 932 and a proximal ring 934 can be laser welded to their respective ends of a flexible portion 936 of the hypotube 442 in order to hold a PTFE tube 938 in place.

Figure 30A:
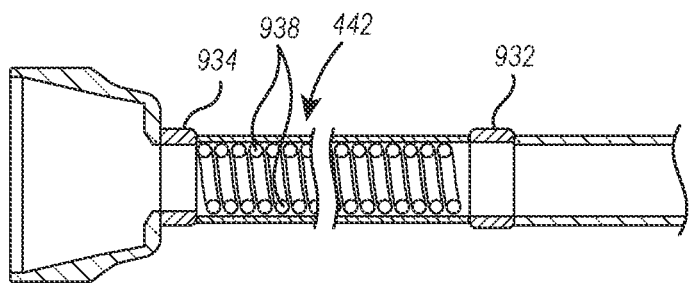
FIGS. 30A to 30D illustrate an alternate embodiment of a delivery catheter for reducing friction between the delivery catheter and the suture catheter.
Figure 30B:
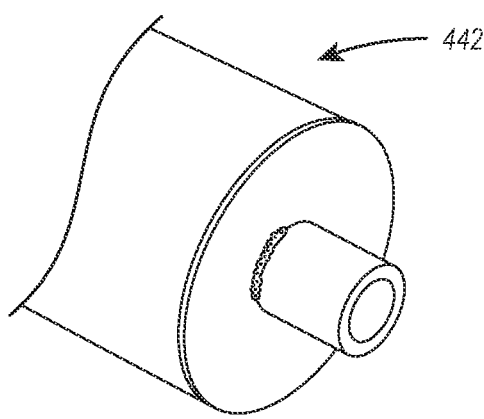
Figure 30C:
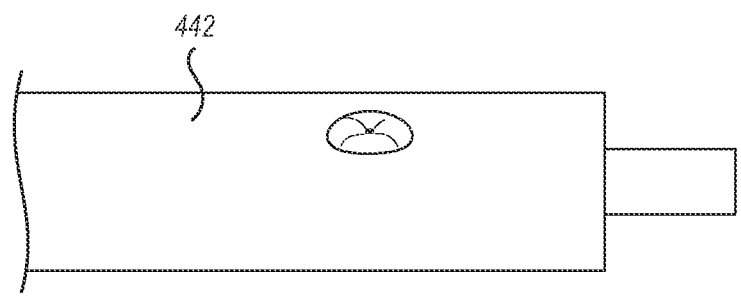
Figure 30D:
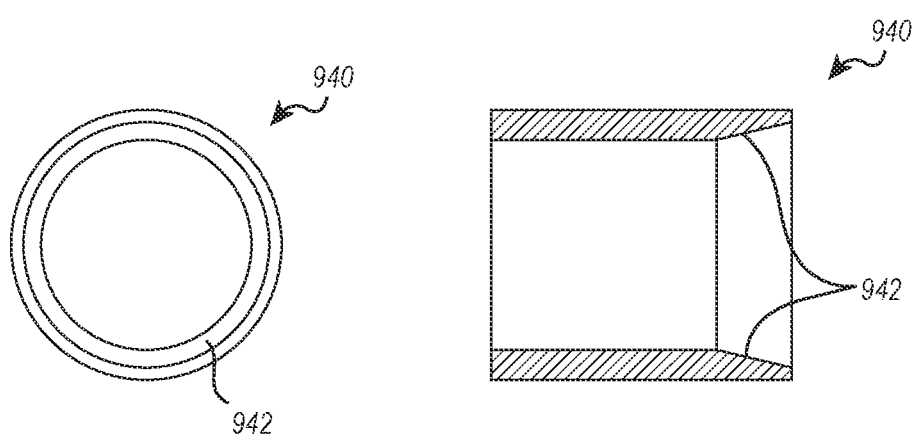

The stiffness of the PTFE tube 938 could also be used to pre-stretch the laser cut pattern of hypotube 442. By adding the "pre-stretch", the hypotube 442 is also able to transmit a reasonable amount of compression force allowing the tube to move forward. A small tube or ring may also be advantageous in that it can be used to center the parts which will be laser welded to the distal and proximal ends of the flexible portion 936. In some embodiments, it may be preferred to avoid the need for a laser weld at the distal and proximal ends of the flexible portion 936 with the PTFE tube 938 which might create a gap if another element, such as a hypotube, is welded to it, as shown in FIG. 30B. In an alternative embodiment, the small tube can be laser welded through the hypotube as shown in FIG. 30C. FIG. 30D shows a front view and a side cross-section view of a small ring 942 laser welded on the interior diameter of a flexible laser cut hypotube to hold an inner liner in place.

Reducing Friction Between Steering Catheter and Outer Sheath

In order to position a valve prosthesis trans-septally, the steering catheter 80 has to be deflected in at least two planes. The deflection angles can be 90° or more for each plane. To release the valve out of the valve cover, high release forces are required. When the outer sheath 82 is pulled back from the proximal end of the delivery system, the forces have to be delivered along the entire length of the delivery system following the sharp bends adjacent the distal end.

In some embodiments, the distal end of a steering catheter 80 can be comprised of a laser-cut hypotube 442 core with a flexible polymer cover (although a braided material may also be used in certain other embodiments). In order to achieve the tight bends 2034, a polymeric material with a low durometer, such as Pebax, and the like, may be preferred. During deployment of the IV device, the outer sheath 82 must be pulled back in a proximal direction relative to the steering catheter 80 (while the position of the steering catheter remains static). Outer sheath 82 can be comprised of a coil braid at its distal end, allowing for flexibility even under high tension and the inner diameter may not ovalize. One disadvantage with this configuration is that the friction between the soft polymer, outer layer of the steering catheter and the coil braid of the outer sheath will increase along the deflected area, thereby requiring a higher pull force. In order to reduce friction between these two catheter layers, a thin coil may be placed over the steering catheter as a metal jacket to reduce said friction.

The addition of a metal jacket 2040 (also referred to as the coil 2040) reduces the friction between the inner metal coil of the outer catheter and the steering catheter will be significantly reduced, thereby allowing a controlled release of the self-expandable valve from the valve cover. The coil 2040 may be designed to withstand the sliding of the outer catheter along its surface without creating any gaps or wings. A 2 or 3-layer construction of the coil 2040 may be preferred over a one-layer construction. The configuration can dictate the degree of deflection, thereby allowing a certain amount of stretch. At the distal end 2044 (FIG. 34), it may be preferred to laser weld the coil 2040 directly to a special designed distal steering ring 2042 which can create a seamless connection between the distal end 2044 and the metal jacket 2040. The proximal end 2046 can be fixed to the outer diameter of the steering catheter by an adhesive such as glue or the like. Alternatively, the proximal end can be heat bonded, for example, by use of a shrink tube applied over the coil followed by the application of heat to fix the shrink tube to the coil, or it can be bounded or laser welded to the proximal section of the inner hypotube.

Flexible Catheter Segment Capable of High Tensile Forces

As described above, transseptal delivery systems require catheter components to be able to bend around multiple out of plane curves where tensile strength is compromised. At the same time, deployment of an IV device requires catheter components, particularly delivery catheter 78, to be able to withstand high tensile strength forces. To enable both input requirements, a short distal component located in the bending region of the delivery system is needed to facilitate both strength and flexibility.

Figure 29:
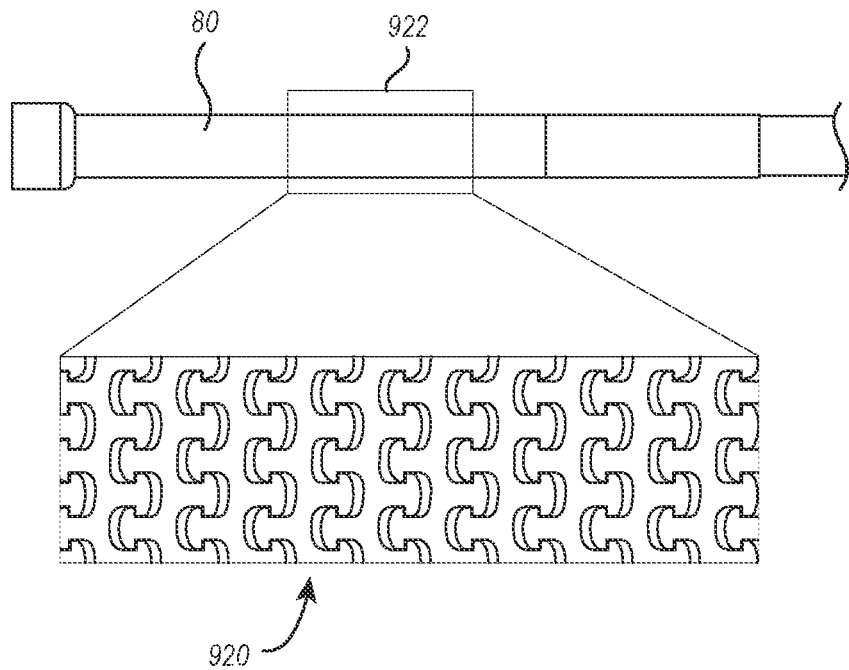
FIG. 29 illustrates a laser cut pattern suitable for hypotube components of the delivery system, which provides flexibility during bending and high tensile and compressive strength when in a straight configuration.

In order to impart adequate strength and flexibility to the delivery catheter 78 and, in some cases, to corresponding sections of other components of the delivery system, a puzzle cut pattern 920, shown in FIG. 29, can be used on a catheter. The pattern, when put under tension or compression in a straight configuration (such as during direct loading or deployment of an IV device, respectively) is capable of withstanding high forces. At the same time, however, the pattern 920 can also provide flexibility and can allow the segment 922 to conform to the curves in multiple planes during valve positioning and release.

Deployment of Collapsed Valve

Deployment of a collapsed valve, such as a mitral valve device, at the mitral annulus requires forces to unsheathe a collapsed mitral valve device from the delivery system to which it is attached. These forces can cause unwanted movement of the delivery system, which can comprise the target location where the valve is intended to be deployed. In order to maintain proper positioning of the valve for deployment, it is necessary to concentrate unsheathing forces to the most distal end of the delivery system without distributing the forces to the curves of the delivery system. A tube screw mechanism or an extension catheter may be used to deploy a collapsed valve contained within a delivery system.

Figure 33:
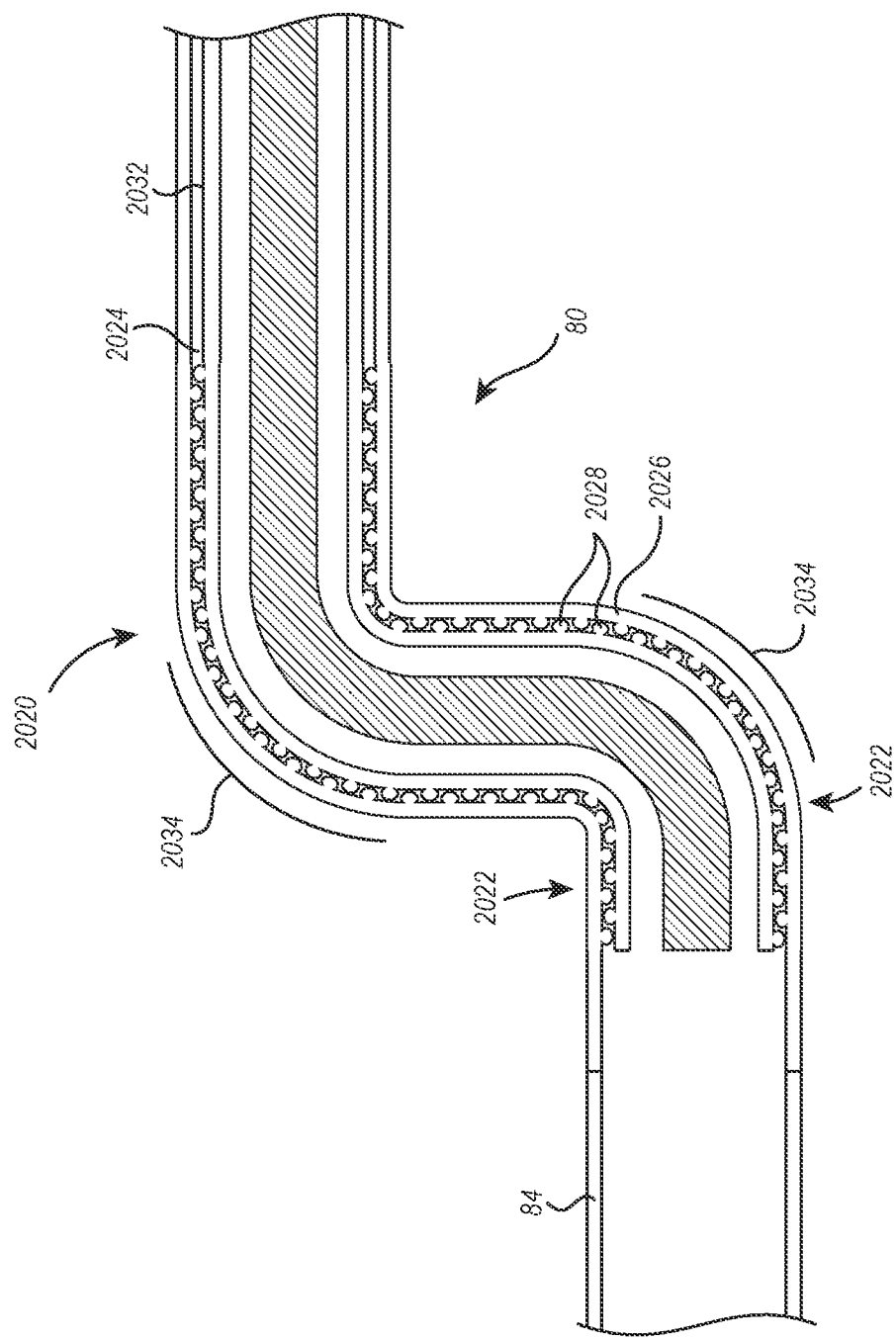
FIG. 33 illustrates an alternate embodiment of an outer sheath for deployment of an IV device.

FIG. 33 illustrates an alternate embodiment of outer sheath 82, incorporating a tube screw mechanism that can be used to pull the valve cover 84 in a proximal direction relative to the other catheter layers of the delivery system without compromising the location or curvature of the such other catheter layers. The tube screw mechanism 2020, as shown in FIG. 33, translates force in a controlled, precise motion to the distal end of of the delivery device. The tube screw mechanism 2020 allows the pullback force to be concentrated to the distal end of the delivery system without affecting the set curves of the delivery system, which position the device for deployment to the mitral annulus.

The tube screw mechanism 2020 of outer sheath 82 can include two hollow tubes that have flexible screws attached to them. The outer torque coil 2022 can include an outer hollow tube 2026 that can be flexible and can have an outer screw 2028 attached to the interior surface of outer hollow tube 2026. The outer screw 2028 can be attached at proximal and distal ends of the inner surface of the outer hollow tube 2026 spanning the bending region of the delivery system. The outer screw 2028 can be flexible in addition to the flexible outer hollow tube 2026. The outer hollow tube 2026 should be able to support compression forces, tensile forces and torsional forces in a compound curve configuration sufficient to provide the forces needed to deploy the IV device.

The inner torque coil 2024 can include a second, inner hollow tube 2032 that can be flexible and can have an inner screw 2030 attached to the outer surface of inner hollow tube 2032. The inner screw 2030 can be attached periodically throughout the working length of the outer surface of inner hollow tube 2032, while still maintaining flexibility. The screw 2030 of the inner torque coil can be flexible. Inner hollow tube 2032 can be flexible as well. The inner hollow tube 2032 should also be able to support compression forces, tensile forces and torsional forces in a compound curve configuration sufficient to provide the forces needed to deploy the IV device.

The outer torque coil 2022 and inner torque coil 2024 can interact to create the tube screw mechanism 2020. This mechanism can result from the inner torque coil 2022 being rotated at its proximal end in a clockwise or counterclockwise direction. Upon rotation, the outer flexible screw 2030 of the inner torque coil 2024 can interact with the inner flexible screw 2028 attached to the outer torque coil 2022, thereby translating the outer torque coil 2022 relative to the inner torque coil 2024 in a proximal or distal direction, depending on the direction of rotation of inner torque coil 2024.

A related embodiment is illustrated in FIG. 35, which illustrates an alternate embodiment of the delivery catheter, namely delivery catheter 2052. In this embodiment, deployment forces are maintained by the delivery catheter 2052 when it is extended distally form the steering catheter 80 and can prevent compression of the delivery catheter 2052 to maintain proper position of the valve 10 as it is delivered to the mitral annulus.

The extension catheter 2052 can have a coil 2054 that can translate back and forth within steering catheter 80 when set in compound curves 2056 to achieve proper positioning of the collapsed valve 10 with respect to the mitral annulus. Delivery catheter 2052 can move distally and proximally relative to steering catheter 80 without compromising the set curves 2056. Delivery catheter 2052 is configured to withstand unsheathing forces during deployment when extended to its maximum distance from the delivery catheter without compressing, kinking, bowing or buckling.

Delivery catheter 2052 may comprise a hollow tube 2058 that can be flexible, and the hollow tube 2058 can be attached to a can 610. The hollow tube 2058 should be able to withstand compression and tensile forces in a compound curve configuration to translate the can 610 in distal and proximal directions, and without shortening lengthening, kinking, bowing, or buckling, to facilitate proper positioning of the IV device 10 within the mitral annulus. The hollow tube 2058 is not compromised after deployment of the valve 10 and can be translated back and forth within the steering catheter 80.

In one embodiment, the coil 2054 of delivery catheter 2052 can include three layers. The inner layer can be comprised of a wire that is wound without a gap between the coil. The inner wire can have various amounts of pretension to contribute to the stiffness of the coil. Increased pretension can contribute to a stiffer coil and can increase its compression strength.

The middle layer can be comprised of multiple wires of the same or similar size wound side by side with no gap between the wires. The number of wires side by side contribute to the stiffness of the coil and increasing the number of wires used increases the stiffness. The middle layer can have various amounts of pretension to contribute to the stiffness of the coil. Increased pretension contributes to a stiffer coil and can increase its compression strength.

The outer layer can be comprised of multiple wires of the same size wound side by side with no gap between the wires. The number of wires side by side contribute to the stiffness of the coil, and increasing the number of wires used increases the stiffness. The outer layer can have various amounts of pretension to contribute to the stiffness of the coil. Increased pretension contributes to a stuffer coil and can increase its compression strength.

The inner and outer layers of the coil can be wound in a clockwise or counterclockwise direction, and both layers may be wound in the same direction. The wound direction of the middle layer can be opposite that of the inner and outer layer. The three layers can be welded together at each end. The amount of welded section can be minimized to maintain flexibility of the coil along the total length.

Detachment Mechanism for Steering Catheter from Steering Box

Figure 31A:
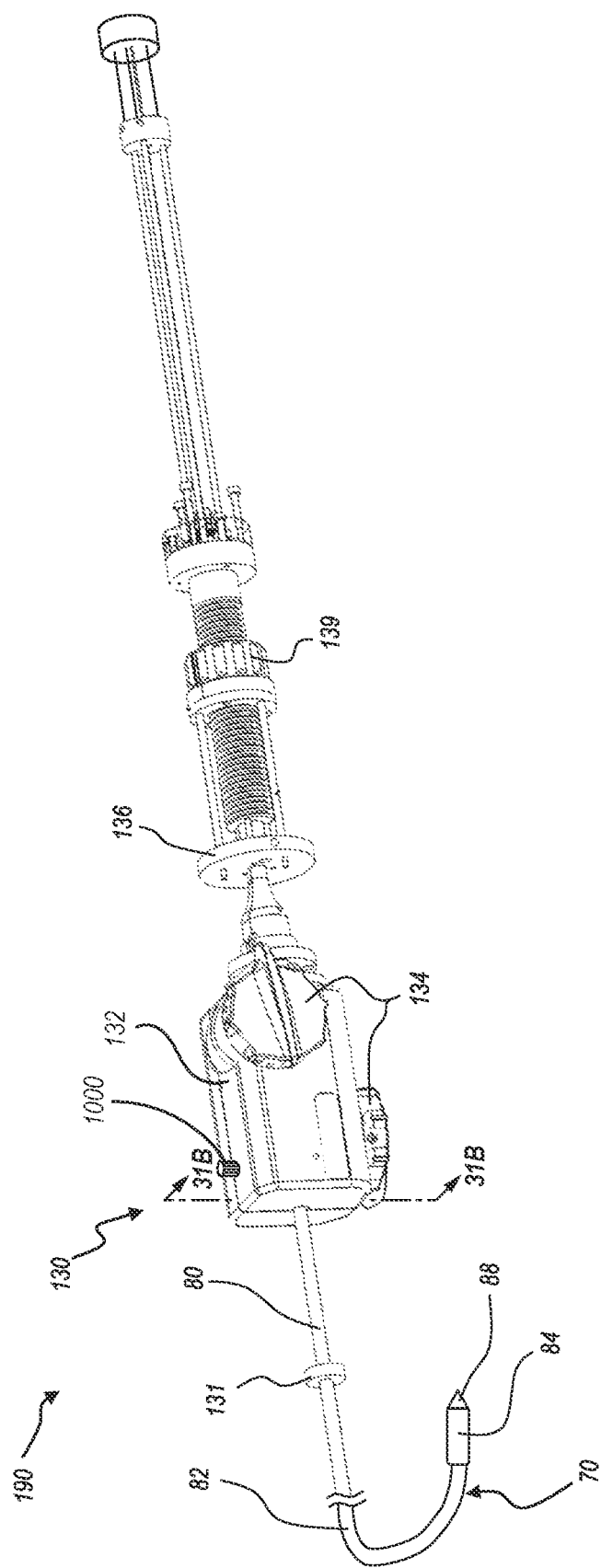
FIG. 31A illustrates a delivery device.
Figure 31B:
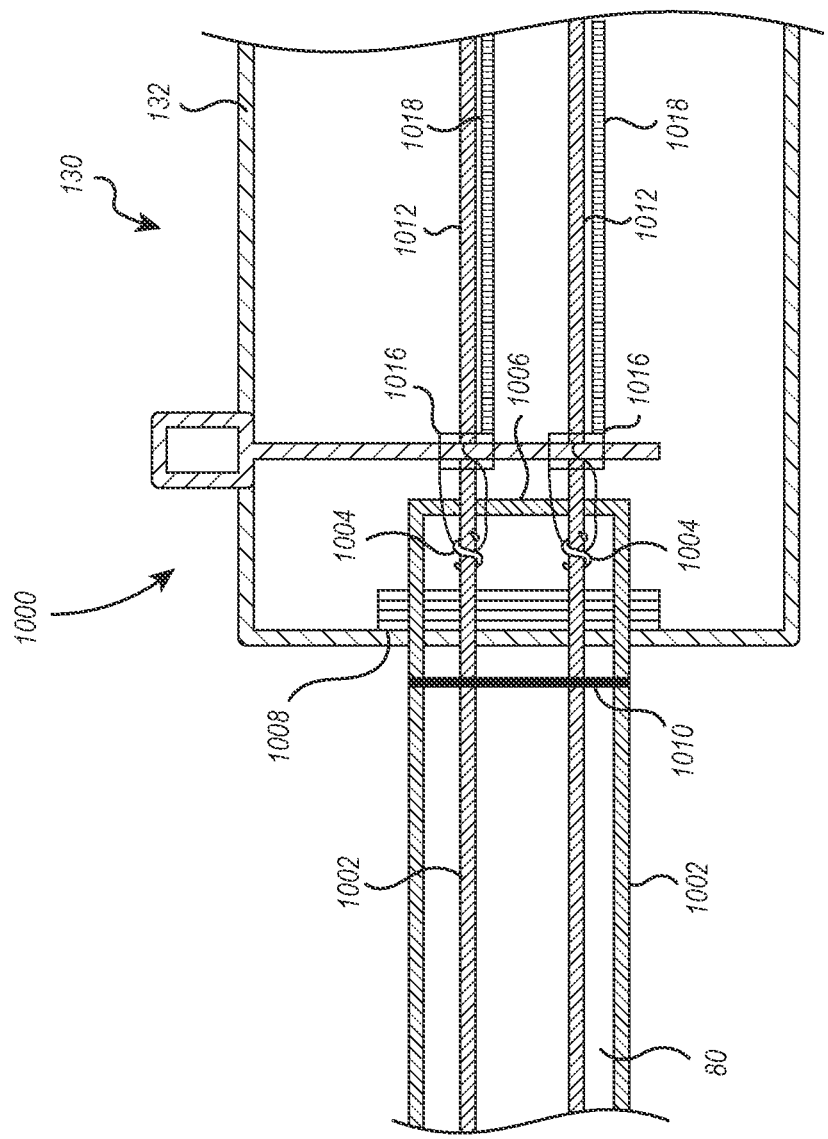
FIG. 31B illustrates an embodiment of a cross-section view of a steering catheter detachment mechanism as shown in FIG. 31A.

The steering catheter 80 as described above can include features to facilitate the removal of the steering catheter 80 from the handle assembly 130 (also referred to herein as steering box 130). The steering catheter detachment mechanism 1000, as schematically described in FIG. 31, can separate the steering catheter 80 from the steering box 130, so that the steering catheter 80 can be disposed of and allow for reuse of the steering box 130.

The steering catheter 80 is used to bend the distal end of the catheter in two directions. The catheter is steered by tensioning cables 1012 in the steering box 130 which extend throughout the length of the steering catheter 80 and attach at the distal end of the catheter 80. The detachment mechanism allows separation of the catheter 80 from the spools 1016 that tighten the cables 1002 to allow removal of the catheter 80 from the steering box 130.

The steering catheter cables 1002 terminate on the proximal end on the catheter 80 with a configuration that can be attached and detached from the steering box cables 1012. The detachment mechanism 1004 can comprise a latch or turning lock that engages the attachment of the cables 1002, for example, with a hoop and loop mechanism, thread, or cable head and slot, or the like. The steering box cables 1012 are positioned by way of an alignment method which can include alignment in slots and/or the distal ends of the steering box cables 1012 stiffed by rods 1018.

A ring 1010 on the proximal end of the catheter 80 can be used to allow the steering cables 1002 to be spread without damage to the cables 1002. The proximal end of the catheter 80 can also include an interfacing component 1006 to seal the inside of the steering box 130 from contamination. A positioning slot 1008 at the interface can be used to align the catheter 80 and steering box 130 to connect the correct cables together.

Catheter Stabilizer Outer Platform

When loading and unloading IV devices into and out of catheters, deflection may occur due to the high forces that are needed to load the IV device into the valve cover and/or deploy the IV device from the valve cover. Deflection is problematic in that it may damage the valve. In some embodiments, an outer platform 3000, disclosed herein and illustrated in FIGS. 36A-36D, can be used with a delivery system to prevent deflection while moving the catheter. The outer platform, which can be situated at the distal end of the handle fixture used to control operation of the delivery system, limits deflection of an intermediate section of the delivery system during the application of high tensile forces through the delivery system during loading of the IV device into the valve cover and/or the application of high compression forces through the delivery system during deployment of the IV device from the valve cover.

The catheter stabilizer outer platform 3000 can be used to telescope the outer catheter to load and unload a valve. A pillar 3002 can be attached to the outer platform 3001 and can include a latch 3010 to connect the platform to the catheter. The pillar 3002 can be attached to the outer platform 3001, which has limited deflection from the slots 3004 in the platform 3001 and in the support 3005.

The outer platform 3001 can include slots 3004 to allow the outer platform 3001 to slide within the support 3005. The slots 3004 can be sized to allow the outer platform 3001 to travel freely within the slot 3004 while limiting upward deflection.

Figure 36A:
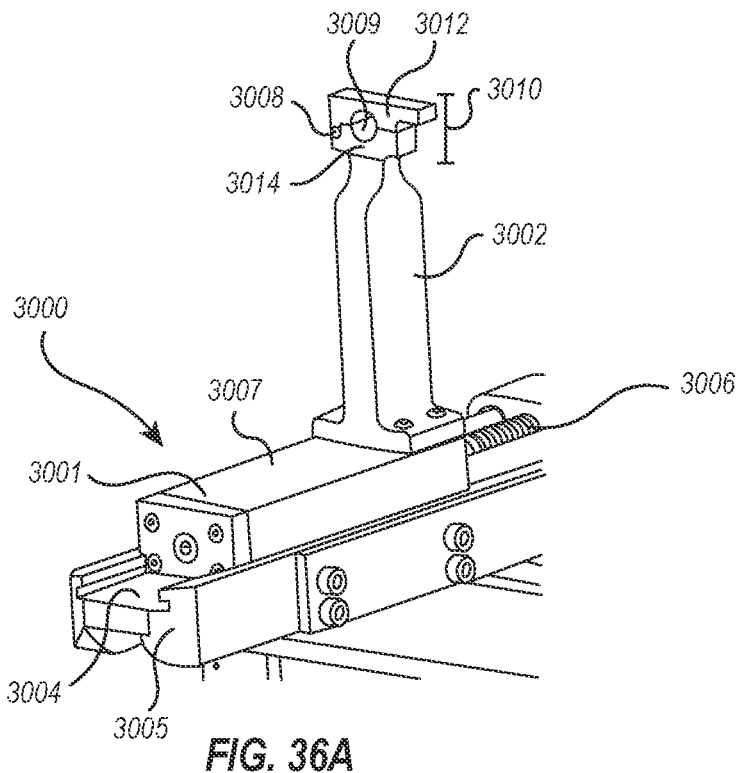
FIGS. 36A to 36D illustrate an embodiment of catheter stabilizer outer platform.
Figure 36B:
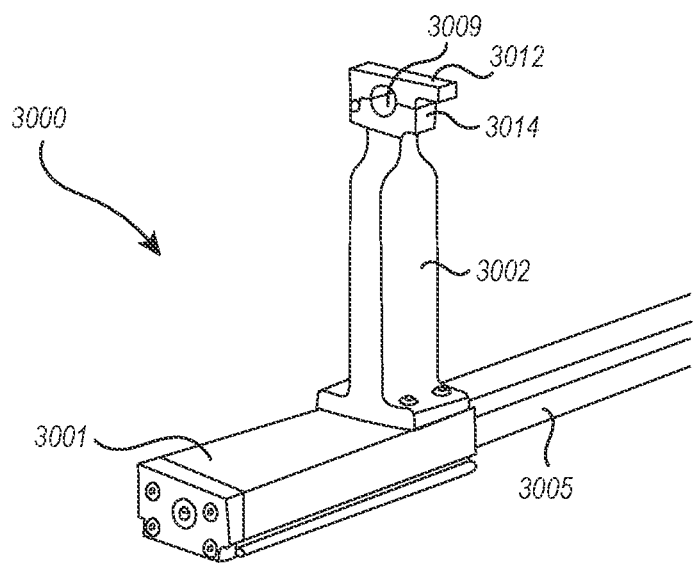
Figure 36C:
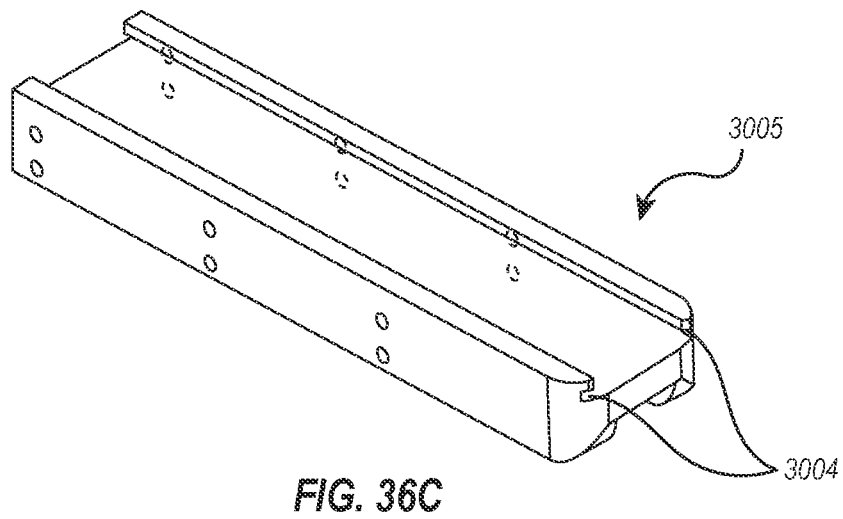
Figure 36D:
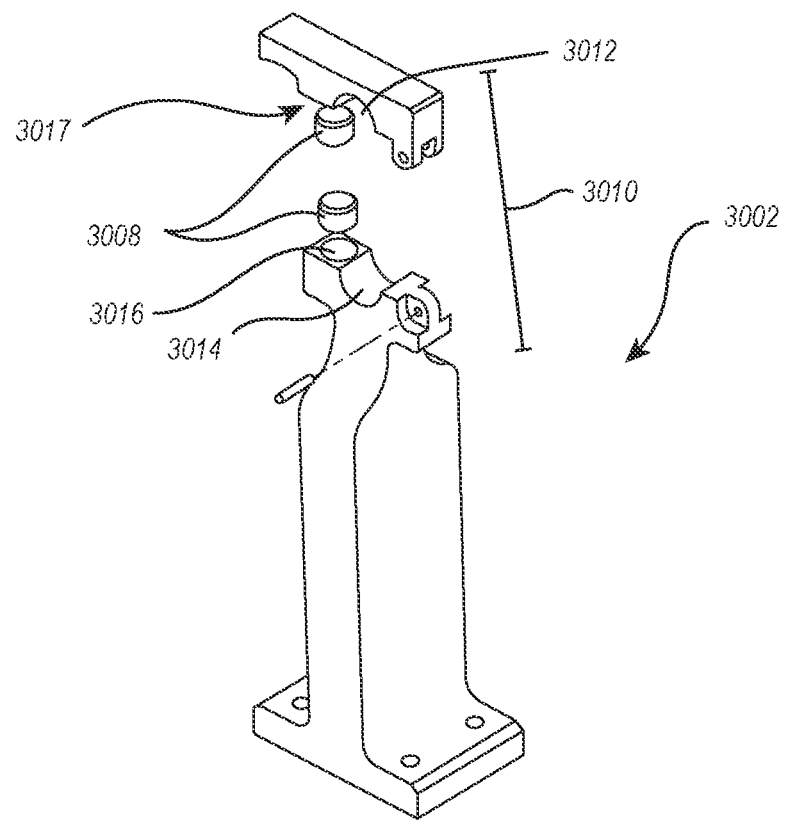

FIG. 36B illustrates the outer platform 3001 extended outward while paired to the support 3005 by way of a connection with the slots 3004. A lead screw 3006, as illustrated in FIG. 36A, can be connected to the outer platform 3001 to generate backwards and forwards motion of the outer platform 3001 along the length of the support 3005. In some embodiments, rails may be included as an attachment to the outer platform 3001 to help navigate the platform 3001 but may not be necessary when the embodiment includes slots 3004.

A pillar 3002 as shown in FIG. 36A, can be configured to interface with a catheter, and can be connected to a top surface 3007 of the outer platform 3001. The pillar 3002 can include a magnetic component 3008 (FIG. 36D) in order to latch on to and maintain control of a catheter inserted therein. The magnets 3008 facilitate quick attachment of the catheter. An annular ring 3009 can be formed by a top latch section 3012 and a bottom latch section 3014 each having a complementary bow shape being oriented in a closed position of the latch 3010 as shown in FIGS. 36A and 36B. Holes 3016, 3017 in the top latch section 3012 and bottom latch section 3014 can be used to house the magnets 3008. Magnets 3008 may be secured by any method that maintains the position of the magnets 3008 separate from each other to allow them to only interact when closing the clamp.

Method for Flushing Percutaneous Valve Delivery System

The present disclosure is directed to methods, systems, and devices for sealing and flushing a catheter to ensure that no air or unwanted fluid is trapped in the catheter when it is delivered through the vasculature of a patient.

As discussed herein, the devices and systems can include a multi-layered elongated delivery member (also referred to herein as simply the elongated member or the delivery member). The delivery member can include a plurality of catheters and/or hypotube members, each of which provides certain functionality during operation of the delivery system to enable effective delivery and deployment of the IV devices. When using a delivery member with multiple components, sufficient flushing of the catheter is necessary before it can be inserted into the vasculature of the human anatomy. As discussed herein, the disclosed delivery systems and devices enable flushing of the various delivery member elements such as the catheter.

The method for prepping a catheter for use requires removing air from the catheter and replacing it with $CO_2$. The air in the prep solution, flush solution, saline, etc., is removed and replaced with $CO_2$. The use of $CO_2$ may be preferred due to its lower solubility in fluids than $O_2$ or $N_2$. $CO_2$ is also more soluble or absorbed into the blood faster than $O_2$ or $N_2$. Bubble reduction in the catheter before it enters the vasculature of the patient reduces the risk of an air bubble being inadvertently released form the device. If an air bubble is released into the patient's blood stream, such as into arterial blood leaving the heart, this could cause myocardial infarctions, stroke or death.

The prep process for a catheter may further include degassing the prep fluid with a vacuum, bubbling in $CO_2$ to saturate the prep fluid. Heating the prep fluid to reduce the solubility of gas in the fluid. This prep process may be done with a system comprising a pump, vacuum chamber, and an air removal membrane such as a gas exchange membrane. Furthermore, the system can be configured with a recirculation tube in order to maintain a closed system as well as continuous flushing of the catheter and delivery system. The system can be automated to control the recirculating time, recirculating flow rate, to pulse or maintain a constant flow, and to control the recirculating pressure.

With reference to the drawings, FIG. 32 illustrates a system and method for flushing the delivery device of FIG. 1, wherein the delivery system 190 may provide one or more additional access points where pressurized line(s) may be connected to introduce a flush fluid or gas into the components of the delivery member 70. The pathways for some of the lumens or the spaces between adjacent components of the deliver member 70 may be especially challenging since the lumens or spaces have dimensions as small as 0.002 inches. Some of these lumens or spaces are used for sutures and wires that will be connected to an intravascular device, such as a valve or repair device, and will enable the loading of the intravascular device as well as the release. It is suggested that all lumen or spaces before they will be flushed with saline or other flushing fluids can be flushed with $CO_2$. The viscosity of a gas compared to a liquid is significantly lower and therefore it will be much easier to replace the entrapped air with a gas like $CO_2$. $CO_2$ is frequently used in medical applications and especially in the peripheral vessels as a contrast medium. The gas, when in contact with blood, will dissolve quickly without causing any air emboli.

In some embodiments, the entire delivery member 190 is flushed with $CO_2$ during production and sealed in a gas tight bag or some other flexible or hard-shell container that will be filled with $CO_2$. This will guarantee that all lumens in the delivery member 190 will be filled with the inert gas and any air emboli can be eliminated. In yet other embodiments, all flush ports will be closed to ensure that the gas will stay in the lumens and spaces. Following packing in an airtight package, the delivery member 190 can be sterilized using, gamma or e-beam. In some embodiments, in order to provide for ETO sterilization, the packaging may be a breathable packaging to allow ETO gas to penetrate the device contained inside of the package. Before use, the delivery member 190 can optionally be flushed with saline solution or can be used directly with the $CO_2$ in the lumens or spaces of the delivery member 190.

Figure 32A:
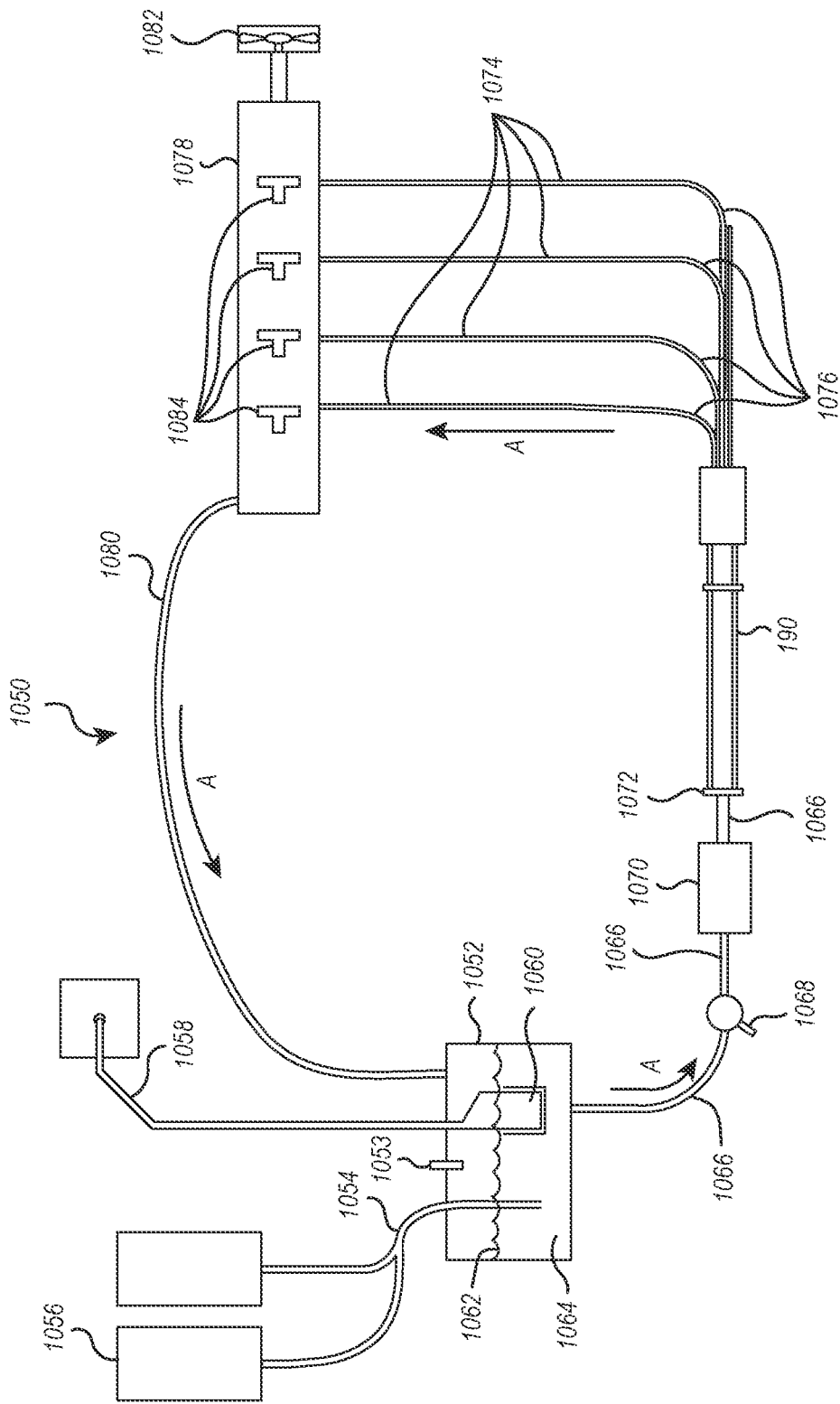
FIG. 32A illustrates a system for flushing the delivery device of FIG. 1.

In one embodiment shown in FIG. 32A, the delivery system 190 is connected to a flushing system 1050. The flushing system 1050 comprises a vacuum chamber 1052 having a fluid line 1054 through which flushing fluids 1064, such as saline, stored in flushing fluid reservoirs 1056 can be delivered to the vacuum chamber 1052. The vacuum chamber 1052 can include a connecting port 1053 which can allow a vacuum source to be connected to the vacuum chamber 1052. The vacuum source will remove $O_2$ and $N_2$ from the chamber 1052 when the flushing fluid 1064 is returned to the chamber 1052 through the recirculating line 1080. The vacuum chamber 1052 can also include a $CO_2$ delivery hose 1058 through which $CO_2$ can be delivered to the vacuum chamber 1052. The delivery hose 1058 can also include a diffuser 1060, such as a microbubble diffuser submerged below the fluid level 1062 of the chamber in order to facilitate the saturation of flushing fluids 1064 with $CO_2$.

Once the flushing fluids 1064 are adequately saturated with $CO_2$, the fluids 1064 travel through hose 1066 to a heater 1070. In some configurations, a pump 1068 may be used to force flushing fluids 1064 through the flushing system 1050. It may be advantageous to heat the flushing fluids 1064 in order to reduce the solubility of gas in the fluid. When the flushing fluids are sufficiently heated, the fluid 1064 is forced through the hose in direction A connected to a port 1072 on the proximal end of the delivery device 190.

The delivery member 70, as described above in FIG. 2, can comprise a number of delivery components including a steering catheter 80 disposed within an outer sheath 82. A delivery catheter 78 disposed within the steering catheter 80.

An inner catheter 72 (or suture catheter 72) disposed within the delivery catheter 78, and a guidewire tube 86 disposed within the inner catheter 72. Alternative embodiments of the delivery member 70 may include different concentric arrangements of constituent parts, as discussed above. The flushing system 1050 is configured to separately flush each component of a delivery member 70 in order to adequately prep the device 190 for a procedure. However, in some embodiments, it may be desirable to use a single tube 1074 to flush the components of the delivery member 70. FIG. 2-2 is a cross-sectional view parallel to the longitudinal axis of a delivery member 70. Each delivery member component can separately be selectively attached to a tube 1074 connected to a stopcock 1078. The stopcock 1078 can have a vent 1082 to allow flushed gasses to escape. The valves 1084 on the stopcock 1078 can be turned to regulate flow or stop flow through a particular delivery member component. The pump 1068 can push the flushing fluid through the delivery device 190, through the components of the delivery member 70, then through the tubes 1074 and into the stopcock 1078, where the excess flushing fluid 1064 is returned to the vacuum chamber 1052 via a recirculating line 1080. This process causes the flushing fluid 1064 to become re-saturated with $CO_2$ and continually passed through the delivery device 190 and delivery member 70 until all $O_2$ and $N_2$ is removed. The flushing system 1050 can be automated by use of a computer system and computer program configured to moderate the flow of the flushing fluid and to sense when the flushing process is complete (i.e. all $O_2$ and $N_2$ is removed).

Figure 32B:
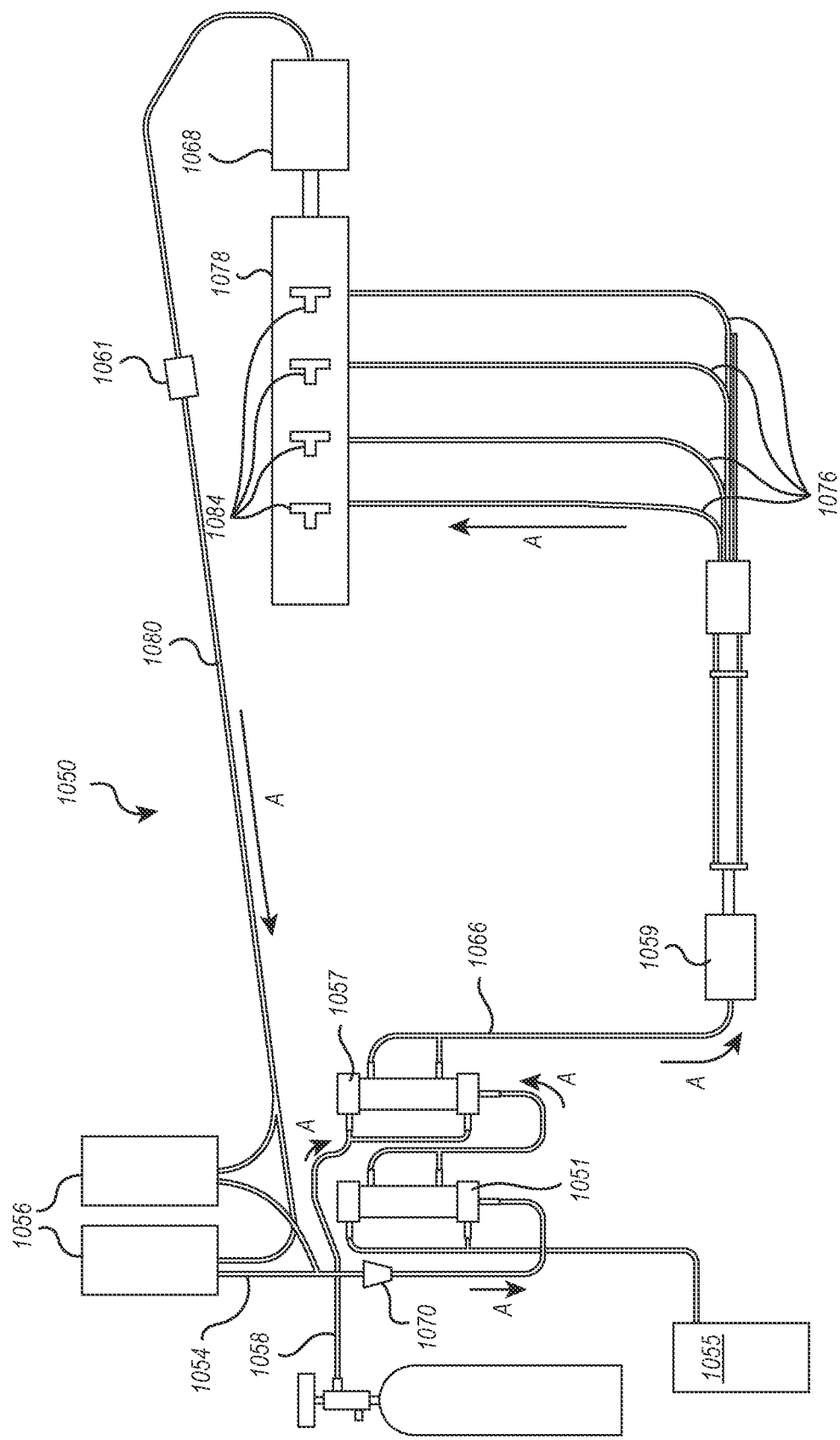
FIG. 32B illustrates an alternate embodiment of a system for flushing the delivery device of FIG. 1.

FIG. 32B illustrates a flushing system 1050 configured as a closed system. The closed system may not have a vacuum chamber 1052, or a similar element providing a gas-fluid interface. Rather, the flushing system 1050 comprises a series of gas exchange tubes 1051,1057, wherein a first gas exchange tube 1051 can be connected to a vacuum pump 1055, and a second gas exchange tube 1057 can be connected to a $CO_2$ delivery hose 1058 through which $CO_2$ can be delivered to exchange tube 1057. Flushing fluids (not shown), such as saline, stored in flushing fluid reservoirs 1056, can be sent from the reservoirs 1056 through a fluid line 1054 to the gas exchange tubes 1051,1057. In the embodiment shown in FIG. 32B, a heating apparatus such as an IV heater 1070 can be used to warm flushing fluids to optimize the gas exchange process.

After passing through the IV heater 1070, the flushing fluid is delivered via a delivery line 1054 to the first gas exchange tube 1051. A vacuum pump 1055 connected to the gas exchange tube 1051 can strip the flushing fluid of gases, such as $O_2$, $N_2$, and $CO_2$, as the flushing fluid is pumped through the gas exchange tube 1051. Once gasses have been removed from the flushing fluid, the flushing fluid can be pumped from the first gas exchange tube 1051 to the second gas exchange tube 1057. The second gas exchange tube 1057 can be connected to a $CO_2$ source by a $CO_2$ delivery hose 1058 which can deliver $CO_2$ to the second gas exchange tube 1057. As flushing fluids are pumped through the second gas exchange tube 1057, the flushing fluids can become saturated with $CO_2$. The gas exchange tubes 1051, 1057 can be hollow fiber gas exchangers made of materials such as silicone, or the like.

The $CO_2$ saturated flushing fluids travel from the second gas exchange tube 1057 through hose 1066 to the delivery device 190. A valve cover seal 1059 can be disposed over the hose 1066 and over the proximal end of the delivery device 190 in order to maintain a closed system and prevent leakage.

Similar to the open flushing system 1050 of FIG. 32A, the flushing system of FIG. 32B is configured to separately flush each component of delivery member 70 in order to adequately prep the device 190 for a procedure. However, in some embodiments, it may be desirable to use a single tube to flush the components of delivery member 70. Each delivery member component can separately be selectively attached to a tube 1074 connected to a stopcock 1078. The valves 1084 on the stopcock 1078 can be turned to regulate flow or stop flow through a particular delivery member component. The pump 1068 can push the flushing fluid through the delivery device 190, through the components of the delivery member 70, then through the tubes 1074 and into the stopcock 1078, where the excess flushing fluid can then be passed through a recirculating line 1080.

The recirculating line 1080 can include an IV filter 1061, such as a 5-micron IV filter, which can filter out particulate matter removed from the device 190 by the flushing fluids during operation of the flushing system 1050. The filtered flushing fluid can then be returned to the flushing fluid reservoir 1056 and then continuously re-circulated through the flushing system until flushing of the device 190 is complete.

Embodiments of the invention, such as the examples disclosed herein, may be beneficial in a variety of respects. For example, and as will be apparent from the present disclosure, one or more embodiments of the invention may provide one or more advantageous and unexpected effects, in any combination, some examples of which are set forth below. It should be noted that such effects are neither intended, nor should be construed, to limit the scope of the claimed invention in any way. It should further be noted that nothing herein should be construed as constituting an essential or indispensable element of any invention or embodiment. Rather, various aspects of the disclosed embodiments may be combined in a variety of ways so as to define yet further embodiments. Such further embodiments are considered as being within the scope of this disclosure. As well, none of the embodiments embraced within the scope of this disclosure should be construed as resolving, or being limited to the resolution of, any particular problem(s). Nor should any such embodiments be construed to implement, or be limited to implementation of, any particular technical effect(s) or solution(s). Finally, it is not required that any embodiment implement any of the advantageous and unexpected effects disclosed herein.

E. Further Example Embodiments

Following are some further example embodiments of the invention. These are presented only by way of example and are not intended to limit the scope of the invention in any way.

Embodiment 1. A delivery system for delivering an IV device to a targeted anatomical site having an elongated delivery member with a plurality of components including an outer sheath with a valve cover at a distal end of the outer sheath for housing the IV device, a steering catheter positioned within the outer sheath, a delivery catheter positioned within the steering catheter, a suture catheter positioned within the delivery catheter and being adapted to maintain a connection with the IV device until deployment of the IV device, a guidewire tube positioned within the suture catheter, and an atraumatic distal tip coupled to a distal end of the guidewire tube, and the delivery system also including a control fixture operatively coupled to, and for controlling the relative movement of the various individual components the elongated delivery member.

Embodiment 2. The delivery system of embodiment 1, wherein the valve cover includes one or more radiopaque or echogenic markers.

Embodiment 3. The delivery system of embodiment 1, wherein the valve cover also has an elongate body portion having a threaded portion at a distal end thereof, and a tip ring having threads complementary of the threaded portion, the tip ring be made of a radiopaque material, and being configured to selectively engage the threaded portion of the elongate body portion in threaded engagement.

Embodiment 4. The delivery system of embodiment 1, wherein the delivery catheter also includes one or more radiographic or echogenic markers at or near a distal end thereof.

Embodiment 5. The delivery system of embodiment 1, wherein the atraumatic distal tip also includes one or more radiographic or echogenic markers embedded therein.

Embodiment 6. The delivery system of embodiment 1, wherein the delivery catheter terminates at a distal end in a can component configured to capture and support a proximal end of the IV device, the can component having an outer diameter, wherein the suture catheter terminates at a distal end in a distal tip ring, and wherein the distal tip ring has in inner diameter smaller than the outer diameter of the can component, to thereby prevent the delivery catheter from being drawn to far in a proximal direction into the delivery system and to provide tactile feedback when the can component of the delivery catheter is seated against the distal tip ring of the steering catheter.

Embodiment 7. The delivery system of embodiment 1, also having a balloon catheter for supporting an inner surface of the IV device during crimping of the IV device to prevent uneven folding of the IV device during a crimping operation.

Embodiment 8. The delivery system of embodiment 1, wherein the atraumatic distal tip can also be selectively attachable to, and selectively detachable from, the guidewire tube.

Embodiment 9. The delivery system of embodiment 1, wherein the delivery catheter has a bending region at or near its distal end, wherein the delivery catheter comprises a laser cut hypotube as part of its bending region, and wherein the delivery catheter also has a PTFE tube attached to an interior surface of the laser cut hypotube to reduce friction between the delivery catheter and the suture catheter.

Embodiment 10. The delivery system of embodiment 1, wherein the steering catheter has a bending region, and wherein the steering catheter also has a HSS coil attached to an outer surface of the steering catheter over the bending region to reduce friction between the steering catheter and the outer sheath.

Embodiment 11. The delivery system of embodiment 1, wherein one or more components of the delivery system can include a laser-cut hypotube having a jig-saw pattern that provides flexibility in bending and high tensile and compressive strength when in a straight configuration or orientation.

Embodiment 12. The delivery system of embodiment 1, wherein the outer sheath can also have an outer tube having an inner surface and a first screw coupled to the inner surface, an inner tube being positioned within the outer tube, the inner tube having an outer surface and a second screw coupled to the outer surface, the second screw being complementary of, and engaging the first screw in threaded engagement, and rotating the inner tube relative to the outer tube causes the outer tube to move in an axial direction.

Embodiment 13. The delivery system of embodiment 1, wherein the steering catheter also has a plurality of control wires or cables used to selectively bend or deflect the steering catheter in one or more planes, wherein the control fixture can also have a steering box operatively connected to the plurality of control wires or cables, the steering box having to or more controls for selectively applying tension to the control wires of cables, and the delivery system also including an attachment interface mechanism for selectively connecting and disconnecting the control wires or cables to the steering box.

Embodiment 14. The delivery system of embodiment 1, wherein the control fixture also has a stabilizer outer platform coupled at a proximal end of the control fixture, the stabilizer outer platform being selectively attachable to the delivery system at a point intermediate the control fixture and the distal end of the delivery system, and providing mechanical support to the delivery system to prevent deflection of the delivery system during the application of high tensile and/or high compressive forces during manipulation of the delivery system.

Embodiment 15. A system for flushing a concentrically arranged, multi-layer catheter delivery system having a vacuum chamber, the vacuum chamber having a vacuum port for connection of a vacuum source to the vacuum chamber, a flushing fluid container, the flushing fluid container containing a flushing fluid, a fluid line, the fluid line having a first end connected to the vacuum chamber, and a second end connected to the flushing fluid container, a delivery hose, the delivery hose having a first end connected to the vacuum chamber, a hose, the hose having a first end connected to the vacuum chamber and a second end connected to a port on a proximal end of the delivery device, at least one or more tubes, wherein a first end of the at least one or more tubes is connected to the delivery member of the delivery device, and wherein a second end of at least one or more tubes is connected to a stopcock, and a recirculating line.

The embodiments summarized above are each combinable with one another, and some embodiments may utilize one or more components from any one of the other embodiments summarized above.

CONCLUSION

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

What is claimed is:

1. A delivery system for delivering an interventional device (IV) device to a targeted anatomical site, the delivery system comprising:
    an elongated delivery member having a proximal end and a distal end configured for housing the IV device, and including a plurality of coaxially positioned delivery member components, the plurality of delivery member components including:
        an outer sheath with a valve cover at a distal end of the outer sheath that is configured to cover the IV device in a collapsed state, the outer sheath comprising:
        a flexible outer tube having an inner surface and a first flexible screw coupled to the inner surface, the first flexible screw being attached at a proximal end and a distal end of a bending region of the outer sheath, the flexible outer tube being configured to support compression forces, tensile forces and torsional forces in a compound curve configuration;
        a flexible inner tube being positioned within the outer tube, the inner tube having an outer surface and a second flexible screw attached periodically throughout a working length of the outer surface of the outer tube, the second screw being complementary of, and engaging the first screw in threaded engagement, whereby rotating the inner tube relative to the outer tube causes the outer tube to move in an axial direction;
        a steering catheter positioned within the outer sheath;
        a delivery catheter positioned within the steering catheter;
        a suture catheter positioned within the delivery catheter and being adapted to maintain a connection with the IV device until deployment of the IV device;
        a guidewire tube positioned within the suture catheter; and
        an atraumatic distal tip coupled to a distal end of the guidewire tube; and
    a control fixture operatively coupled to the proximal ends of, and for controlling the relative movement of, the outer sheath, the steering catheter, the delivery catheter, the suture catheter and the guidewire tube.

2. The delivery system of claim 1, wherein the valve cover includes one or more radiopaque or echogenic markers.

3. The delivery system of claim 1, wherein the valve cover further comprises:
    an elongate body portion having a threaded portion at a distal end thereof; and
    a tip ring having threads complementary of the threaded portion, the tip ring be made of a radiopaque material, and being configured to selectively engage the threaded portion of the elongate body portion in threaded engagement.

4. The delivery system of claim 1, wherein the delivery catheter includes one or more radiographic or echogenic markers at or near a distal end thereof.

5. The delivery system of claim 1, wherein the atraumatic distal tip includes one or more radiographic or echogenic markers embedded therein.

6. The delivery system of claim 1, wherein the delivery catheter terminates at a distal end in a can component configured to capture and support a proximal end of the IV device, the can component having an outer diameter, wherein the suture catheter terminates at a distal end in a distal tip ring, and wherein the distal tip ring has in inner diameter smaller than the outer diameter of the can component, to thereby prevent the delivery catheter from being drawn to far in a proximal direction into the delivery system and to provide tactile feedback when the can component of the delivery catheter is seated against the distal tip ring of the steering catheter.

7. The delivery system of claim 1, further comprising a balloon catheter for supporting an inner surface of the IV device during crimping of the IV device to prevent uneven folding of the IV device during a crimping operation.

8. The delivery system of claim 1, wherein the atraumatic distal tip is selectively attachable to, and selectively detachable from, the guidewire tube.

9. The delivery system of claim 1, wherein the delivery catheter has a bending region at or near its distal end, wherein the delivery catheter comprises a laser cut hypotube as part of its bending region, and wherein the delivery catheter further comprises a PTFE tube attached to an interior surface of the laser cut hypotube to reduce friction between the delivery catheter and the suture catheter.

10. The delivery system of claim 1, wherein the steering catheter has a bending region, and wherein the steering catheter further comprises a coil attached to an outer surface of the steering catheter over the bending region to reduce friction between the steering catheter and the outer sheath.

11. The delivery system of claim 1, wherein one or more components of the delivery system comprises a laser-cut hypotube having a jig-saw pattern that provides flexibility in bending and high tensile and compressive strength when in a straight configuration or orientation.

12. The delivery system of claim 1, wherein the steering catheter further comprises a plurality of control wires or cables used to selectively bend or deflect the steering catheter in one or more planes, wherein the control fixture further comprises a steering box operatively connected to the plurality of control wires or cables, the steering box having two or more controls for selectively applying tension to the control wires of cables, and further comprising an attachment interface mechanism for selectively connecting and disconnecting the control wires or cables to the steering box.

13. The delivery system of claim 1, wherein the control fixture further comprises: a stabilizer outer platform coupled at a proximal end of the control fixture, the stabilizer outer platform being selectively attachable to the delivery system at a point intermediate the control fixture and the distal end of the delivery system, and providing mechanical support to the delivery system to prevent deflection of the delivery system during the application of high tensile and/or high compressive forces during manipulation of the delivery system.

14. A system for flushing a delivery system, the system comprising:
- a delivery system for delivering an interventional device; and
- a flushing system, the flushing system comprising:
  - a vacuum chamber,
    - the vacuum chamber having a vacuum port for connection of a vacuum source to the vacuum chamber;
  - a flushing fluid container, the flushing fluid container containing a flushing fluid received from a fluid reservoir,
  - a diffuser disposed in the flushing fluid container and submerged below a fluid level of the flushing fluid in the flushing fluid container, the diffuser being in fluid communication with and receiving carbon dioxide from a source of carbon dioxide, the diffuser being configured to saturate the flushing fluid in the flushing fluid container with carbon dioxide from the source of carbon dioxide;
  - a fluid line,
    - the fluid line having a first end connected to the vacuum chamber, and a second end connected to the flushing fluid container;
  - a delivery hose, the delivery hose having a first end connected to the vacuum chamber;
  - a hose, the hose having a first end connected to the vacuum chamber and a second end connected to a port on a proximal end of the delivery system;
  - at least one or more tubes, wherein a first end of the at least one or more tubes is connected to a delivery member of a delivery system, and wherein a second end of at least one or more tubes is connected to a stopcock, and
  - a recirculating line,
  - wherein a first end of the recirculating line is connected to the stopcock, and wherein a second end of the recirculating line is connected to the vacuum chamber.

15. The system for flushing of claim 14, wherein the delivery system comprises:
- the delivery member having a proximal end and a distal end configured for housing an interventional device (IV) device, and including a plurality of coaxially positioned delivery member components, the plurality of delivery member components including:
  - an outer sheath with a valve cover at a distal end of the outer sheath;
  - a steering catheter positioned within the outer sheath;
  - a delivery catheter positioned within the steering catheter;
  - a suture catheter positioned within the delivery catheter and being adapted to maintain a connection with the IV device until deployment of the IV device;
  - a guidewire tube positioned within the suture catheter; and
  - an atraumatic distal tip coupled to a distal end of the guidewire tube; and
- a control fixture operatively coupled to the proximal ends of, and for controlling the relative movement of, the outer sheath, the steering catheter, the delivery catheter, the suture catheter and the guidewire tube.

* * * * *